(12) United States Patent
Hsu et al.

(10) Patent No.: US 8,083,758 B2
(45) Date of Patent: Dec. 27, 2011

(54) METHODS AND DEVICES FOR TREATING OBESITY AND GERD BY INTUSSUSCEPTING A PORTION OF STOMACH TISSUE

(75) Inventors: Charles S. Hsu, Palo Alto, CA (US); Darin H. Buxbaum, Palo Alto, CA (US); Fan Zhang, Mountain View, CA (US); Ivan T. Tzvetanov, Palo Alto, CA (US); Jennifer T. Blundo, Palo Alto, CA (US)

(73) Assignee: HourGlass Technologies, Inc., Redwood City, CA (US)

( * ) Notice: Subject to any disclaimer, the term of this patent is extended or adjusted under 35 U.S.C. 154(b) by 887 days.

(21) Appl. No.: 11/870,096

(22) Filed: Oct. 10, 2007

(65) Prior Publication Data

US 2008/0255592 A1 Oct. 16, 2008

Related U.S. Application Data

(60) Provisional application No. 60/854,167, filed on Oct. 26, 2006.

(51) Int. Cl.
*A61B 17/08* (2006.01)

(52) U.S. Cl. ........................................ 606/153; 606/151

(58) Field of Classification Search .................. 606/139, 606/159, 151, 153, 232; 623/23.65, 23.64; 128/898
See application file for complete search history.

(56) References Cited

U.S. PATENT DOCUMENTS

| | | |
|---|---|---|
| 5,088,979 A | 2/1992 | Filipi et al. |
| 5,403,326 A | 4/1995 | Harrison et al. |
| 5,787,897 A | 8/1998 | Kieturakis |
| 5,887,594 A | 3/1999 | LoCicero, III |
| 6,117,148 A | 9/2000 | Ravo et al. |
| 6,254,642 B1 * | 7/2001 | Taylor ........................ 623/23.64 |
| 6,312,437 B1 | 11/2001 | Kortenbach |
| 6,447,533 B1 | 9/2002 | Adams |
| 6,494,888 B1 | 12/2002 | Laufer et al. |
| 6,543,456 B1 | 4/2003 | Freeman |

(Continued)

FOREIGN PATENT DOCUMENTS

WO  WO-02/096327 A2  12/2002

(Continued)

OTHER PUBLICATIONS

Supplementary European Search Report mailed on Sep. 22, 2008, for European Patent Application No. 04 81 6031, filed on Dec. 30, 2004, two pages.

(Continued)

*Primary Examiner* — Tuan Nguyen

(74) *Attorney, Agent, or Firm* — Morrison & Foerster LLP

(57) ABSTRACT

Described here are devices and methods for intussuscepting a portion of stomach tissue. Typically the intussusception is created at a position near, but distal to the gastroesophageal junction, and a pouch capable of storing a volume (from about 0 cc up to about 100 cc) is created proximal the intussuscepted tissue. In this way, the amount of food that may be ingested is reduced, helping to ameliorate GERD symptoms, and aiding in weight loss efforts. Some of the devices described here include an expandable member and at least one suction inlet. In these devices, the expandable member is expanded to create a proximal cavity into which the stomach tissue is pulled (e.g., using suction), thereby creating the intussusception.

19 Claims, 20 Drawing Sheets

U.S. PATENT DOCUMENTS

| | | | |
|---|---|---|---|
| 6,558,400 | B2 | 5/2003 | Deem et al. |
| 6,572,629 | B2 | 6/2003 | Kalloo et al. |
| 6,663,639 | B1 | 12/2003 | Laufer et al. |
| 6,736,828 | B1 | 5/2004 | Adams et al. |
| 6,746,460 | B2 | 6/2004 | Gannoe et al. |
| 6,790,214 | B2 | 9/2004 | Kraemer et al. |
| 6,837,894 | B2 | 1/2005 | Pugsley, Jr. et al. |
| 6,884,250 | B2 | 4/2005 | Monnasevitch et al. |
| 6,937,894 | B1 | 8/2005 | Isaac et al. |
| 6,981,978 | B2 | 1/2006 | Gannoe |
| 6,994,715 | B2 | 2/2006 | Gannoe et al. |
| 7,047,981 | B2 | 5/2006 | Durgin |
| 7,074,229 | B2 | 7/2006 | Adams et al. |
| 7,076,305 | B2 | 7/2006 | Imran et al. |
| 7,083,629 | B2 | 8/2006 | Weller et al. |
| 7,094,247 | B2 | 8/2006 | Monassevitch et al. |
| 7,097,650 | B2 | 8/2006 | Weller et al. |
| 7,120,498 | B2 | 10/2006 | Imran et al. |
| 7,121,283 | B2 | 10/2006 | Stack et al. |
| 7,152,607 | B2 | 12/2006 | Stack et al. |
| 7,153,314 | B2 | 12/2006 | Laufer et al. |
| 7,220,284 | B2 | 5/2007 | Kagan et al. |
| 7,261,722 | B2 * | 8/2007 | McGuckin et al. ........... 606/139 |
| 7,674,271 | B2 | 3/2010 | Bjerken |
| 2001/0020190 | A1 | 9/2001 | Taylor |
| 2002/0183768 | A1 | 12/2002 | Deem et al. |
| 2004/0024427 | A1 | 2/2004 | Imran et al. |
| 2004/0039452 | A1 | 2/2004 | Bessler |
| 2004/0193184 | A1 | 9/2004 | Laufer et al. |
| 2004/0225183 | A1 | 11/2004 | Michlitsch et al. |
| 2004/0225305 | A1 | 11/2004 | Ewers et al. |
| 2004/0230137 | A1 | 11/2004 | Mouton |
| 2004/0243195 | A1 | 12/2004 | Imran et al. |
| 2005/0070931 | A1 | 3/2005 | Li et al. |
| 2005/0075654 | A1 | 4/2005 | Kelleher |
| 2005/0080444 | A1 * | 4/2005 | Kraemer et al. ............ 606/192 |
| 2005/0085923 | A1 | 4/2005 | Levine et al. |
| 2005/0143760 | A1 | 6/2005 | Imran |
| 2005/0149072 | A1 | 7/2005 | DeVries et al. |
| 2005/0149114 | A1 * | 7/2005 | Cartledge et al. ............ 606/213 |
| 2005/0192599 | A1 | 9/2005 | Demarais |
| 2005/0192601 | A1 | 9/2005 | Demarais |
| 2005/0228504 | A1 | 10/2005 | Demarais |
| 2005/0240279 | A1 | 10/2005 | Kagan et al. |
| 2005/0247320 | A1 | 11/2005 | Stack et al. |
| 2005/0251176 | A1 | 11/2005 | Swanstrom et al. |
| 2005/0272968 | A1 | 12/2005 | Byrum et al. |
| 2006/0020277 | A1 | 1/2006 | Gostout et al. |
| 2006/0069400 | A1 | 3/2006 | Burnett et al. |
| 2006/0135971 | A1 | 6/2006 | Swanstrom et al. |
| 2006/0142790 | A1 | 6/2006 | Gertner |
| 2006/0151568 | A1 | 7/2006 | Weller et al. |
| 2006/0178562 | A1 | 8/2006 | Saadat et al. |
| 2006/0190018 | A1 | 8/2006 | Baker et al. |
| 2006/0252983 | A1 | 11/2006 | Lembo et al. |
| 2006/0253131 | A1 | 11/2006 | Wolniewicz, III |
| 2006/0253142 | A1 * | 11/2006 | Bjerken ........................ 606/153 |
| 2006/0271076 | A1 | 11/2006 | Weller et al. |
| 2007/0005080 | A1 | 1/2007 | Wolniewicz, III et al. |
| 2007/0005082 | A1 | 1/2007 | Kraemer et al. |
| 2007/0073318 | A1 | 3/2007 | Carter et al. |
| 2007/0073323 | A1 | 3/2007 | Carter et al. |
| 2007/0088373 | A1 | 4/2007 | Baker |
| 2007/0112363 | A1 | 5/2007 | Adams |
| 2007/0129738 | A1 | 6/2007 | Kraemer et al. |
| 2009/0062820 | A1 | 3/2009 | Hsu et al. |

FOREIGN PATENT DOCUMENTS

| | | |
|---|---|---|
| WO | WO-2004/021894 A1 | 3/2004 |
| WO | WO-2004/037064 A2 | 5/2004 |
| WO | WO-2004/037064 A3 | 5/2004 |
| WO | WO-2005/058239 A2 | 6/2005 |
| WO | WO-2005/058239 A3 | 6/2005 |
| WO | WO-2005/065412 A2 | 7/2005 |
| WO | WO-2005-065412 A3 | 7/2005 |
| WO | WO-2005/097012 A2 | 10/2005 |
| WO | WO-2005/097012 C1 | 10/2005 |
| WO | WO-2007/041598 A1 | 4/2007 |

OTHER PUBLICATIONS

International Preliminary Report on Patentability mailed on May 7, 2009, for PCT Application No. PCT/US2007/021737, filed on Oct. 10, 2007, five pages.

International Search Report mailed on Mar. 3, 2008, for PCT Application No. PCT/US2007/021737, filed Oct. 10, 2007, six pages.

Written Opinion mailed on Mar. 3, 2008, for PCT Application No. PCT/US2007/021737, filed on Oct. 10, 2007, six pages.

Awan, A.N. et al. (2002). "Endoscopic Vertical Band Gastroplasty With An Endoscopic Sewing Machine," *Gastrointestinal Endoscopy* 55(2):254-256.

European Communication mailed on Nov. 9, 2010, for European Patent Application No. 07839460.8, filed on Oct. 10, 2007, three pages.

Filipi, C.J. et al. (2001). "Transoral, Flexible Endoscopic Suturing for Treatment of GERD: A Multicenter Trial," *Gastrointestinal Endoscopy* 53(4):416-422.

First Office Action for Chinese Application No. 200780048196.X, mailed on Dec. 28, 2010, filed on Oct. 10, 2007, three pages, English Translation.

Jennings, R.W. et al. (Oct. 1992). "A Novel Endoscopic Transgastric Fundoplication Procedure for Gastroesophageal Reflux: An Initial Animal Evaluation," *Journal of Laparoendoscopic Surgery* 2(5):207-213.

Kadirkamanathan, S.S. et al. (1999). "An Ambulant Porcine Model of Acid Reflux Used to Evaluate Endoscopic Gastroplasty," *Gut* 44:782-788.

MEDICINENET.COM. (1999-2010). "Definition of Intussusception," located at <http://medterms.com/scipt/main/art.asp?articlekey=4028,> last visited on Oct. 5, 2010, two pages.

Non-Final Office Action mailed on Jun. 21, 2011, for U.S. Appl. No. 12/265,539, filed on Nov. 5, 2008, eight pages.

Non-Final Office Action mailed on Apr. 1, 2011, for U.S. Appl. No. 12/265,509, filed on Nov. 5, 2008, seven pages.

* cited by examiner

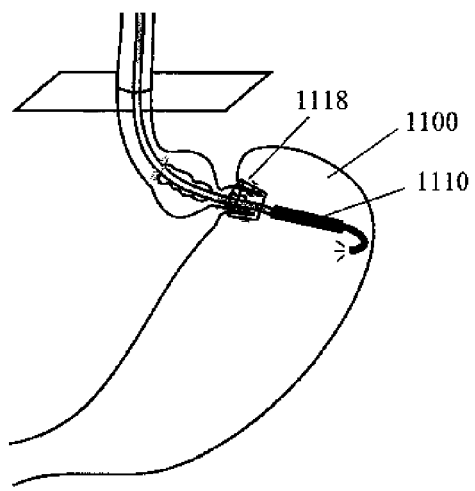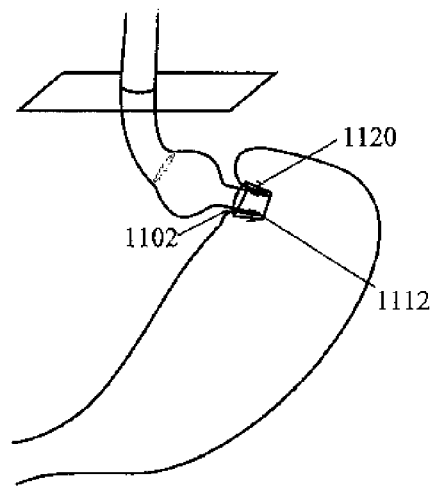
Fig. 11I
Fig. 11J

METHODS AND DEVICES FOR TREATING OBESITY AND GERD BY INTUSSUSCEPTING A PORTION OF STOMACH TISSUE

CROSS-REFERENCE TO RELATED APPLICATIONS

This application claims priority to U.S. Provisional Patent Application Ser. No. 60/854,167 filed on Oct. 26, 2006, which is hereby incorporated by reference in its entirety.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

Obesity and gastroesophageal reflux disease (GERD) both impact a substantial number of people in society. Therapies exist to treat these diseases; however, many of the current therapies have limitations that result in only a sub segment of the market receiving treatment. Spurred by the continuing growth of these diseases, new therapies are being developed to address these limitations.

Current therapies for obesity range in invasiveness and efficacy. The least invasive therapies include diet, exercise, and pharmaceuticals. These therapies have not yet shown significant weight loss over the long-term. More invasive treatment options include weight loss surgeries, such as gastric bypass, vertical banded gastroplasty, and adjustable gastric banding. These procedures share at least one common element, namely, restricting stomach size. These procedures have shown long-term weight loss, but carry significant surgery-associated risks.

New devices are being developed to achieve the efficacy of weight loss surgery, while employing less invasive procedures. These devices utilize mechanisms of action that include restricting stomach size, stimulating the stomach (e.g., using electrical stimulation), filling a portion of the stomach with a space-occupying member, and introducing one or more malabsorptive elements into the stomach. While the invasiveness of the weight loss procedures has been reduced, the new mechanisms of action remain to be clinically proven. Additionally, many of the new weight loss devices are large and bulky, which reduces ease of use and may lead to long procedure times.

In addition, treatment of GERD follows a progression of therapies. Initially, lifestyle modifications, which include changes to diet, are utilized. If symptoms persist, the next level of treatment is typically pharmacologic therapies, which range from antacids to proton pump inhibitors. These therapies tend to be tolerated over the long-term. For more severe cases of GERD, or for cases where patients seek a one-time treatment, surgery may be required. The most common surgical procedure is fundoplication, which has good efficacy but carries the inherent risks of surgery.

Similar to new obesity treatments, new GERD treatments seek to obtain the efficacy of surgery but in a less invasive manner. These therapies seek to reduce the esophageal aperture via mechanisms of action including radio frequency ablation, esophageal cinching, and tissue plication.

Due to the great need in the areas of obesity and GERD, the development of additional less invasive device solutions is desirable.

BRIEF SUMMARY OF THE INVENTION

Described here are devices and methods for intussuscepting a portion of stomach tissue. Typically the intussusception is created at a position near, but distal to the gastroesophageal junction, and a pouch capable of storing a volume anywhere from 0 cc up to about 100 cc is created proximal to the intussuscepted tissue. In this way, the amount of food that may be ingested is reduced, helping to ameliorate GERD symptoms, and aiding in weight loss efforts. In addition, the gastric reduction volume can provide negative feedback to reduce the desire to eat.

In some variations, the devices comprise an expandable member and at least one suction inlet. In these variations, the expandable member is expanded to create a proximal cavity into which the stomach tissue is pulled (e.g., using suction), thereby creating the intussusception. The devices typically comprise a main shaft, having a lumen therethrough, through which an endoscope or other suitable device may be advanced. The expandable member may or may not be releasably attached to the main shaft of the device. It should be understood that some variations of the devices described here do not employ an expandable member or suction.

The devices may further comprise one or more anchor introducers for housing one or more anchors therein, which can be deployed through the anchor introducers, and thereby secure the intussuscepted tissue. The one or more anchor introducers are typically radially expandable (e.g., by an expandable balloon, expandable cage, one or more radially expanding prongs, or the like) to position the anchor introducers adjacent to the intussuscepted tissue. Any number of anchor introducers may be used for housing any suitable number and type of anchors (e.g., T-tags, V-tags, H-tags, etc.). The devices may further comprise a protecting portion to limit movement of the anchor introducers.

The devices may also comprise a retaining material, e.g., to help secure the intussuscepted tissue. In some variations, one or more anchors are configured to pierce through the retaining material, helping to secure the intussusception. The retaining material may or may not be positioned about at least an inner portion of the expandable member, may or may not be continuous, may or may not have a uniform thickness, and may or may not be adjustable.

The devices may also comprise a sizing component for sizing a pouch to be created proximal to the intussuscepted tissue, in order to limit the amount of food that may be consumed. In some variations the devices described here further comprise a retractable sheath that covers at least a distal portion of the device.

Methods for intussuscepting a portion of stomach tissue are also provided. In some variations, the methods comprise creating an intussusception with stomach tissue distal to a gastroesophageal junction and deploying one or more anchors through the intussuscepted tissue to secure the intussusception. In some variations, the intussusception is created in a single step. The anchors may or may not be deployed through the intussuscepted tissue simultaneously, and may or may not be positioned adjacent to the intussuscepted tissue simultaneously. The methods may further comprise positioning at least one retaining material adjacent to the intussusception prior to deploying one or more anchors through the intussuscepted tissue. In these variations, the one or more anchors are most typically deployed through at least a portion of the retaining material.

A pouch is created proximal to the intussuscepted tissue, which serves to reduce the amount of food capable of being consumed. The pouch may be of any suitable size and is typically capable of retaining any volume, from 0 cc up to about 100 cc of volume. The volume of the pouch may be controlled or otherwise determined using a sizing component, such as an expandable balloon.

The intussusception may be created in any suitable manner, and in some variations, it is created by suction. For example, in some variations, it is created by transorally advancing a device to a position distal to a gastroesophageal junction, where the device comprises an expandable member and a suction inlet. The intussusception may then be created with the expandable member and suction.

BRIEF DESCRIPTION OF THE DRAWINGS

FIGS. 11A-11J depict an illustrative method of creating an intussusception in a portion of stomach tissue.

DETAILED DESCRIPTION OF THE INVENTION

I. Overview and Anatomy

Described here are devices and methods for treating obesity and GERD by intussuscepting a portion of the stomach. The intussusception is created at a target location distal of the gastroesophageal junction, such that a small pouch, able to contain a volume from 0 cc up to about 100 cc of volume, is left proximal the intussuscepted tissue. As used herein, the terms "intussuscept," "intussusception," "intussuscepting," and the like refer to the creation of a continuous tissue fold created by telescoping one part of the stomach onto or into another part of the stomach. The devices enable (though need not be used in such a fashion) tissue intussusception in a single step, which could greatly reduce procedure time.

Figure 1A:
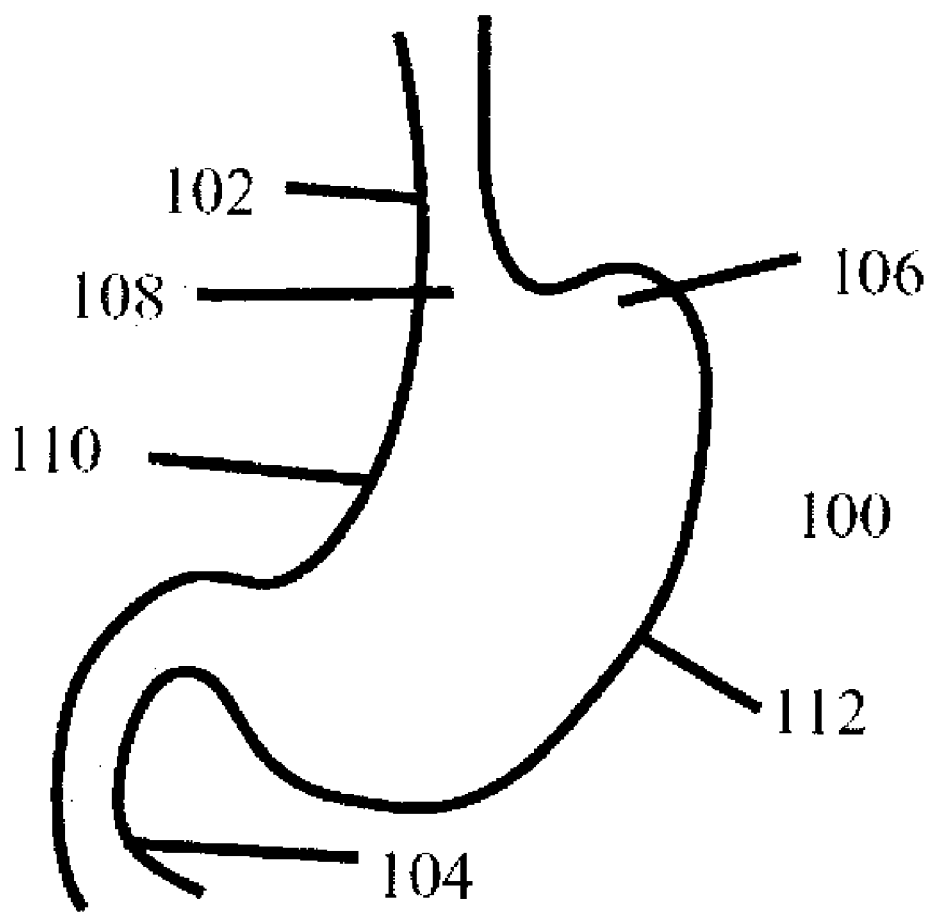
FIG. 1A shows a simplified depiction of the human stomach.
Figure 1B:
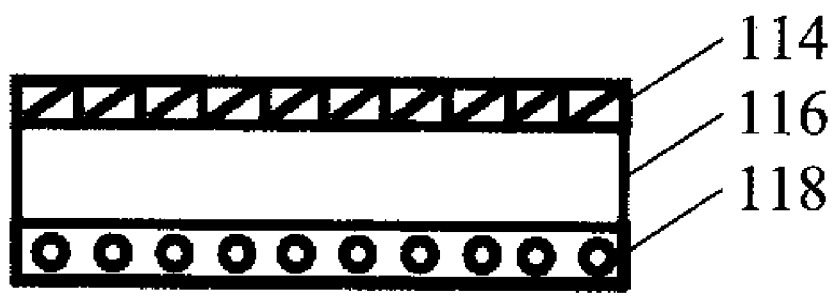
FIG. 1B provides a cross sectional view of the various stomach layers.

FIG. 1A shows a simplified depiction of stomach (100) and its surrounding anatomy. Shown there is esophagus (102) and duodenum (104) in fluid communication with stomach body at its proximal and distal ends respectively. Also shown is fundus (106), gastroesophageal junction (108), and lesser and greater curvatures (110) and (112) respectively. FIG. 1B provides a simplified cross sectional view of the various stomach layers. Shown there is serosa layer (114), muscle layer (116), and mucosa layer (118).

II. Devices

The devices for treating obesity and GERD described here serve to intussuscept a portion of the stomach and to secure the stomach in its intussuscepted configuration. Some of the devices described here comprise an expandable member and at least one suction inlet, where the expandable member is expanded to create a proximal cavity into which the stomach tissue is pulled using suction, thereby creating the intussusception. In other of the devices described here, expandable members and suction are not used to create the intussusception. One or more anchors may be deployed to secure the intussusception, with or without a retaining band or other material, as will be described in detail below.

Figure 2:
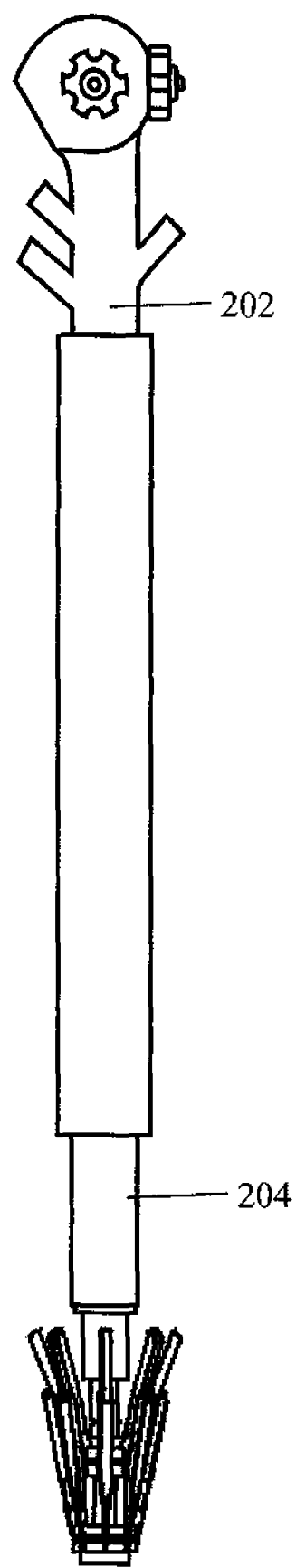
FIG. 2 shows an overview of an illustrative device described here.

FIG. 2 shows an overview of device (200) having proximal portion (202) and distal portion (204). Distal portion (204) is shown in greater detail in FIGS. 3A and B and various proximal portions are described in greater detail with reference to FIGS. 9A, 9B, and 9C.

Figure 3A:
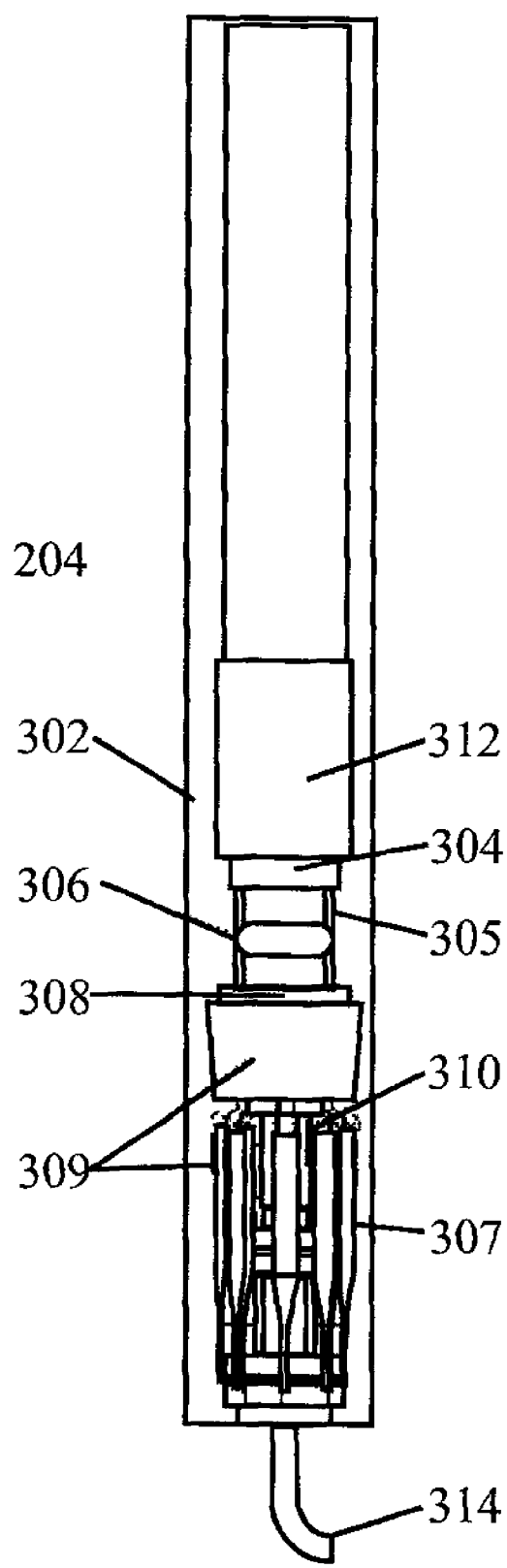
FIGS. 3A and 3B provide detailed depictions of a distal portion of a device described here, having a collapsed and an expanded configuration respectively.

Shown in FIG. 3A is one variation of distal portion (204), including sheath (302), holder (304), anchor introducers (305), anchor introducer expander (306), main shaft (307), retaining material (308), expandable member (309), and sizing component (312). In this variation, sheath (302) covers most of distal portion (204), and is slidable with respect to distal portion (204). In this way, the device (200) may be advanced in a low profile manner to a target site of interest. The sheath may also serve to protect the individual components of the device (200) from disrupting esophageal tissue while the device (200) is advanced to a target location transorally. While shown in FIG. 3A as having a length that covers most of distal portion (204), the sheath (302) need not have such a length. Indeed, the sheath (302) may only cover a portion of distal portion (204), and in some variations, the sheath (302) only covers or partially covers expandable member (309). In other variations, the device simply does not comprise a sheath. When a sheath is used, it may be made of any suitable biocompatible material, and is most typically in the form of a flexible tube (e.g., a polymeric tube, such as one made of polyesters, polyimides, polyurethanes, combinations thereof, and the like). The sheath may also comprise one or more metals, which may be formed in any suitable fashion (e.g., braided metallic ribbons, coils, and the like). Suitable metals include, but are not limited to, stainless steel, aluminum, nickel-titanium alloys, and combinations thereof. In some variations, when the sheath (302) is withdrawn proximally, sizing component (312) and/or the expandable member (309) automatically expands. In these variations, the sizing component and/or the expandable member is made of a self-expandable material, as will be described in more detail below. The sheath (302) is shown partially withdrawn or proximally retracted in FIG. 3B.

Holder (304) is configured to hold, house, couple to or with, or otherwise engage anchor introducers (305) at their proximal ends (or at their proximal portions). Holder (304)

should be made of a biocompatible material, and is typically in the form of a flexible tube. The holder may be made of the same or different materials, than those of the sheath. Anchor introducers (305) may be held or otherwise attached to holder (304) in any suitable manner. For example, the anchor introducers (305) may be held in grooves formed in holder (304), the grooves having shapes corresponding to the shapes of the outer surfaces of the anchor introducers (305). The anchor introducers (305) may be snap-fit into or with the holder (304), but need not be. Indeed, the anchor introducers may simply be held in a friction-fit fashion between the grooves in the holder (304) and the main shaft (307) of the device. The anchor introducers (305) may also be attached to the holder (304) mechanically (e.g., using pins, screws, etc.), by using glue or other adhesives, or the like. The anchor introducers may also be housed within a portion of the expandable member, or a housing off the expandable member (309).

Figure 3B:
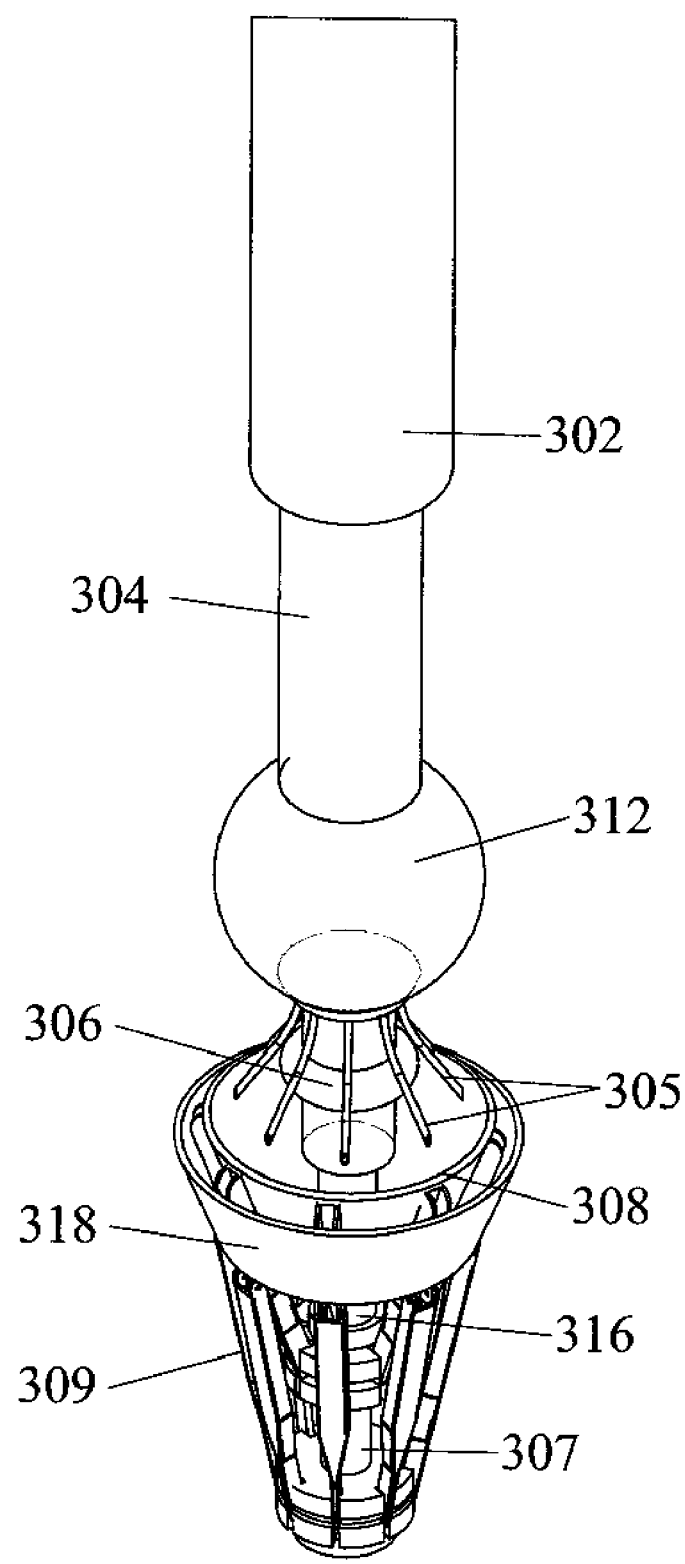

The anchor introducers (305) shown in FIG. 3A have tissue-piercing tips, but the tips need not be tissue-piercing and the tips need not be pointed. They may be blunt, or may have points with one or more beveled surfaces thereon. The anchor introducers (305) are typically made of a flexible material having a lumen capable of housing one or more anchors therein, although it should be understood that the anchor introducers need not be made of a flexible material. The anchor introducers may be made of the same or different materials, than those of the sheath. In some variations, the anchor introducers (305) are made of stainless steel hypotubes. While two anchor introducers (305) are shown in FIG. 3A and five are shown in FIG. 3B, any number of anchor introducers (305) may be used (e.g., 1, 2, 3, 4, 5, 6, or more). In some variations the device comprises one anchor introducer (305). In other variations, the device comprises six or more anchor introducers (305). Also, while the anchor introducers (305) are shown in FIGS. 3A and 3B as having the same length, the anchor introducers (305) may have different lengths, and may be arranged in any suitable configuration. For example, the anchor introducers (305) may be uniformly spaced or non-uniformly spaced, and may or may not be spatially layered (i.e., the tips or ends of the anchor introducers may be closer or further from the main shaft (307)).

Figure 3C:
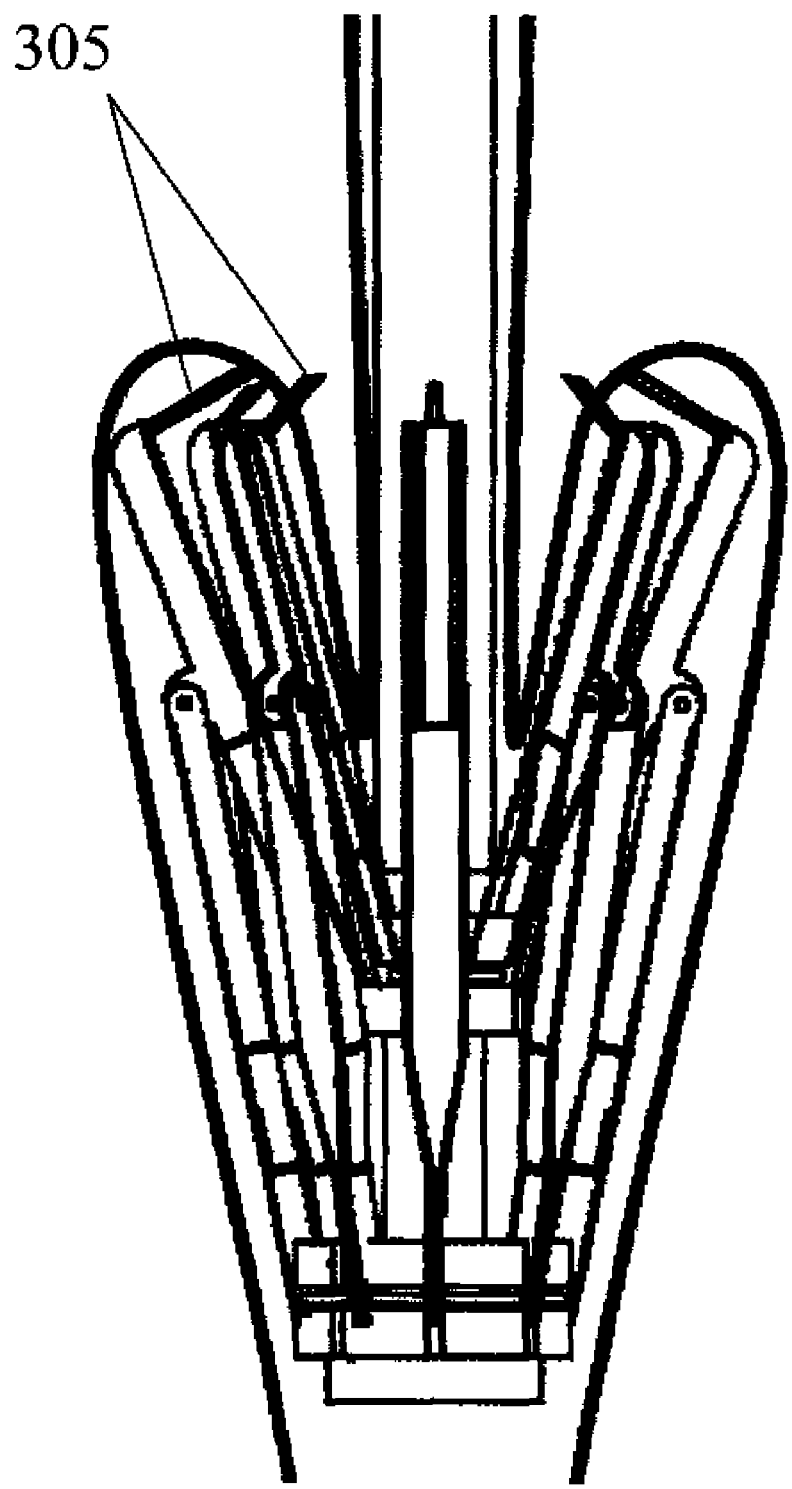
FIG. 3C provides an illustration of one variation of an expandable member.

The anchor introducers (305) are typically configured to radially expand and pierce through an intussusception, although as noted above, the anchor introducers need not be configured to pierce through tissue (e.g., may instead be used to position the anchors prior to deployment). In the variation shown in FIGS. 3A and 3B, the anchor introducers (305) are also configured to pierce through at least a portion of retaining material (308), and are expanded by anchor introducer expander (306). After at least a portion of the retaining material (308) has been pierced by the anchor introducers (305), one or more anchors are deployed therethrough, as will be described in more detail below with reference to the methods. FIG. 3C depicts an alternate placement for the anchor introducers (305) where they are positioned at the ends of an expandable member (309). The anchor introducer expander (306) may be any suitable component capable of aiding the radial expansion of the one or more anchor introducers (305). For example, the anchor introducer expander (306) may be a balloon (as shown in the variation of FIGS. 3A and 3B), an expandable cage, one or more radially expanding prongs, or the like. The anchor introducer expander (306) may also be a pulley system, a pulling mechanism, or the like. It need not be a single component as depicted in FIGS. 3A and 3B.

The retaining material (308) should be made of a material capable of retaining the stomach tissue in its intussuscepted configuration. For example, the retaining material may be made of an elastomeric material, such as biocompatible rubbers, polyurethanes, polyesters, nylons, etc.), may be made of a super-elastic or shape memory material (e.g., nickel-titanium alloys and the like), or may be made of other suitable materials. The material may be porous (e.g., mesh like, or woven in nature), or may not be. The retaining material may be continuous, or may be non-continuous in nature (e.g., made from more than one interconnected or interlocked pieces). All, or any portion of the retaining material may be coated, impregnated, or otherwise include a radiopaque or echogenic tag or marker to aid in visualization. The material may be configured for permanent placement in a stomach (i.e., be biocompatible and able to withstand stomach acids and the stomach environment generally) or be configured for temporary placement (i.e., be made of a biodegradable material). In instances where sufficient fibrosis is expected to occur, the retaining material may be configured to degrade over time, leaving a permanent fibrosed intussuscepted configuration. In some variations, the retaining material (308) is configured for permanent placement and is made of a continuous band of material as shown in FIGS. 3A and 3B. As will be described in more detail with reference to FIGS. 4A-4F, the retaining material (308) may be of any suitable shape, be continuous or non-continuous, and have a uniform or non-uniform thickness. In the variation shown in FIGS. 3A and 3B, retaining material (308) is positioned along at least an inner portion of expandable member (309), such that when expandable member (309) is expanded, and at a least a portion of the stomach is intussuscepted into a proximal cavity of the expandable member (309), the retaining material (308) abuts the intussuscepted tissue and retains the intussuscepted configuration when one or more anchors are placed therethrough.

The devices described here may further comprise a sizing component (312), shown in its delivery configuration in FIG. 3A and its deployed configuration in FIG. 3B. The sizing component (312) helps to position the distal portion (204) of the device past the gastroesophageal junction, and also serves to ensure that there is enough stomach volume above the intussuscepted tissue. The sizing component (312) may also help facilitate the placement of the distal portion of the device relative to the stomach wall (e.g., by helping with angle positioning, etc.). In some variations, such as the variation shown in FIGS. 3A and 3B, the sizing component (312) is a balloon. The sizing component (312) may also be an expandable cage, one or more radially expandable prongs, or the like, and may be manually expanded or self-expanding with the removal of the sheath (302).

Also shown in FIG. 3A is suction line (310) with suction inlet (316), and endoscope (314). The suction line (310) is configured to provide suction to stomach tissue to create the intussusception. While shown in FIG. 3A as located adjacent to main shaft (307), the suction line (310) and suction inlet (316) may be placed at any convenient location capable of making the intussusception. As shown in FIG. 3B, the suction inlet (316) is positioned centrally with respect to the expandable member (308). This variation may be desirable to help ensure proper suction of the stomach tissue to create an intussusception of suitable depth while minimizing risk of obstruction. Any number of suction lines (310) and suction inlets (316) may be used. Alternatively, in variations where the endoscope (314) already has a port that enables suction, the endoscope may be positioned adjacent to the suction inlet (316) to provide a suction channel for helping to create an intussusception.

Endoscope (314) may be any suitable endoscopic device to provide for visualization during the creation and securing of the intussusception. For example, the endoscope may be a pediatric endoscope, or similar endoscope having a low profile. Other scopes or devices may also be inserted through, or alongside of, the lumen of main shaft (307), if desirable or useful.

FIG. 3B shows distal portion (204), where sheath (302) has been partially retracted, and sizing component (312), expandable member (309), and anchor introducer expander (306) are all shown in expanded or partially expanded configurations. The devices described here may also comprise a protective portion (318), which is also shown in FIG. 3B. Protective portion (318) may be useful to prevent anchor introducers (305), or anchors, from penetrating too deeply into or through the stomach tissue. For example, the protective portion (318) serves to prevent the anchor introducers (305) from puncturing through to the outside of the stomach wall, where the puncturing is not associated with the securing of the intussusception (it should be understood that the anchor introducer pierces through to the outside of the stomach wall during the securing of the intussusception, as will be discussed in more detail with reference to the methods). Protective portion (318) also prevents anchors from being deployed adjacent to a serosal layer. Protective portion (318) is shown in FIG. 3B as a continuous band of material, though it need not be. For example, the protective portion may be folded in a fan-shape so that, e.g., it may be expanded when the expandable member is fully expanded, or may be a thin flab of a metallic material, that is attached to the expandable member, or components thereof. Alternatively, the protective portion may comprise a safety mechanism in the anchor introducers or expandable member that limits deployment of anchor introducers or anchors, to a safe range. The protective portion may be made of any suitable material. For example, the protective portion may be made of one or more polymers, e.g., polystyrene, polypropylene, polyethylene (such as high-density polyethylene, ultrahigh molecular weight polyethylene, and the like), KEVLAR®, etc. Similarly, the protective portion may be made of one or more metals (e.g., stainless steel, aluminum, or the like). The protective portion may also be made of a combination of materials (e.g., a combination of one or more polymers and metals, etc.). In some variations, e.g., where a portion of the expandable member (309) serves the above functions, the protective portion (318) may not be necessary.

Figure 4A:
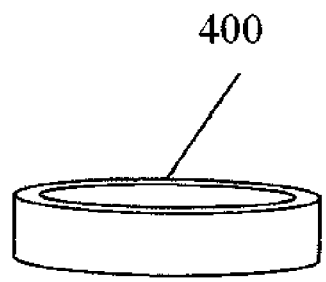
FIGS. 4A-4F provide illustrative variations of suitable retaining materials for use with the devices and methods described here.
Figure 4B:
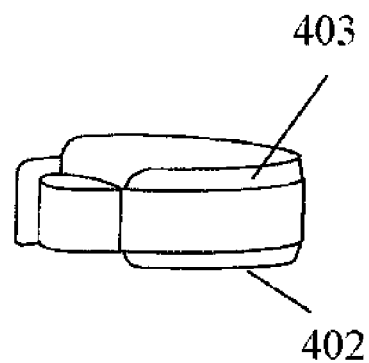
Figure 4C:
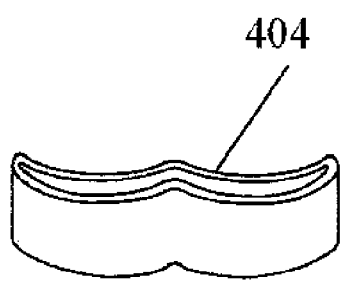
Figure 4D:
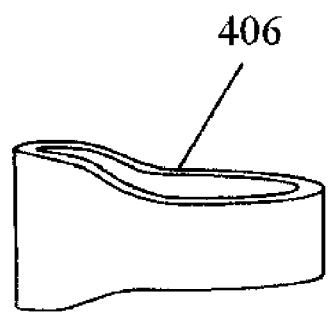
Figure 4E:
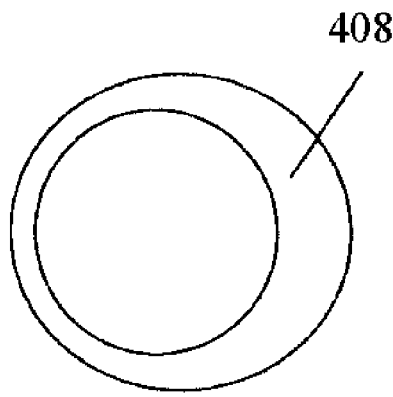
Figure 4F:
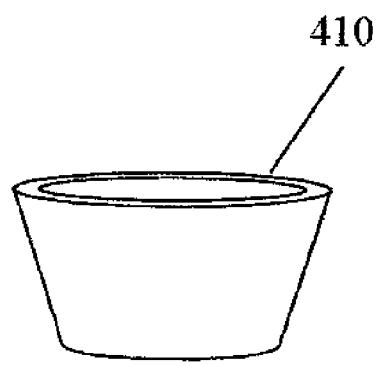

As mentioned briefly above, the retaining material may have any suitable geometry or configuration, and may be continuous or discontinuous. FIGS. 4A-4F provide various depictions of suitable retaining materials. Shown in FIG. 4A is a variation of retaining material (400) in the form of a continuous band of material having a uniform diameter. FIG. 4B is an illustration of retaining material (402) having an inflatable portion (403). FIGS. 4C and 4D provide side views of variations of retaining materials having a non-uniform thickness, and FIG. 4E provides a top view of a variation having a non-uniform thickness. FIG. 4F depicts a retaining material (410) having a generally conical configuration (and the conical configuration can be applied to any suitable shape). The retaining material may or may not be adjustable (either in length, height, or thickness) in situ. In variations where the retaining material is adjustable, the retaining material may comprise one or more inflation cavities or lumens, and adjustability may be achieved by filling (and thus inflating) the one or more cavities or lumens with a space filling substance or member (e.g., water, saline, air, carbon dioxide, etc.). The retaining material may also be made adjustable by use of a ratcheting mechanism, on or in combination with, the retaining material. In addition, the retaining material may or may not have one or more portions resistant to puncture or piercing by the anchor introducers or by the anchors themselves. For example, one surface (e.g., outer surface) of the retaining material may be made of a non-puncturable material (e.g., a relatively rigid material). One or more surfaces of the retaining material (308), or a part thereof, may be transparent, translucent, radiolucent, echolucent, or the like to aid in visualization (either endoscopically, or with an alternative device, such as with ultrasound).

Figure 5:
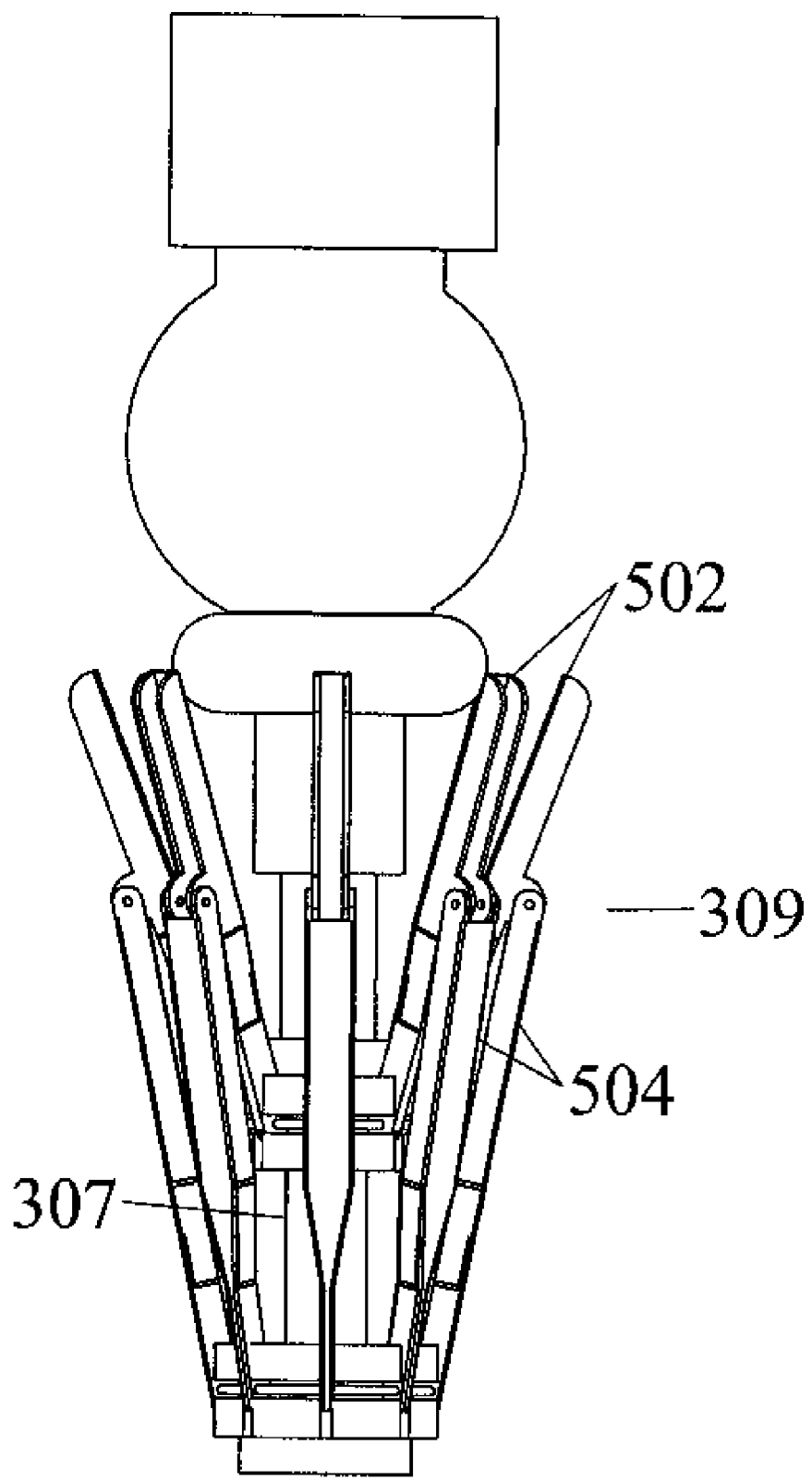
FIG. 5 provides a close-up illustration of an expandable member that may be used with the devices and methods described here.

FIG. 5 provides a close-up illustration of an expandable member (309), suitable for use with the devices and methods described herein. In this variation, the expandable member (309) comprises a series of radially expanding prongs. Any number of prongs may be used. While the prongs shown here are equally spaced apart, they need not be. Indeed, the spacing between the prongs may or may not be uniform. In addition, the prongs may be asymmetrically be deployed, be of different lengths, and may expand radially at individually differing angles (e.g., to aid in the creation of an intussusception of suitable depth and geometry). The prongs may thus be positioned to form any suitable geometry, e.g., an oval, a circle, etc. It should also be understood, that when the prongs of FIG. 5 are fully expanded, portions (502) and (504) are angled away from the main shaft (307), this need not be so. Indeed, in other variations, one or more of portions (502) and (504) are parallel with or angled towards the main shaft (307) when fully expanded. In the variations shown here, the expandable member may be hyper expanded, such that the prongs flip over and collapse, leading to a collapsible configuration for easy release of a retaining material, should it be used, and withdrawal of the device. In addition, while the expandable member (309) is shown having two portions (502) and (504), the expandable member may be monolithic in nature, comprising a single unitary body. A transparent, translucent, or opaque material may cover at least a portion of the expandable member (309), if desirable.

The device may further comprise one or more locking mechanisms to lock the expandable member in an expandable configuration. The expandable member may also be re-usable. In these variations, the expandable member is configured for releasable attachment or coupling to the main shaft (307), and is made of a sterilizable material. In these variations, the remainder of the device may or may not be disposable. As mentioned briefly above, the expandable member may also be configured for self-expansion upon proximal withdrawal of the sheath. In these variations, the expandable member is made of a shape memory material, such as shape memory alloys (e.g., a nickel titanium alloy or the like) or shape memory polymers, or is made of a material having sufficient elasticity, such that it will spring to its expanded configuration when the sheath is withdrawn.

Figure 6A:
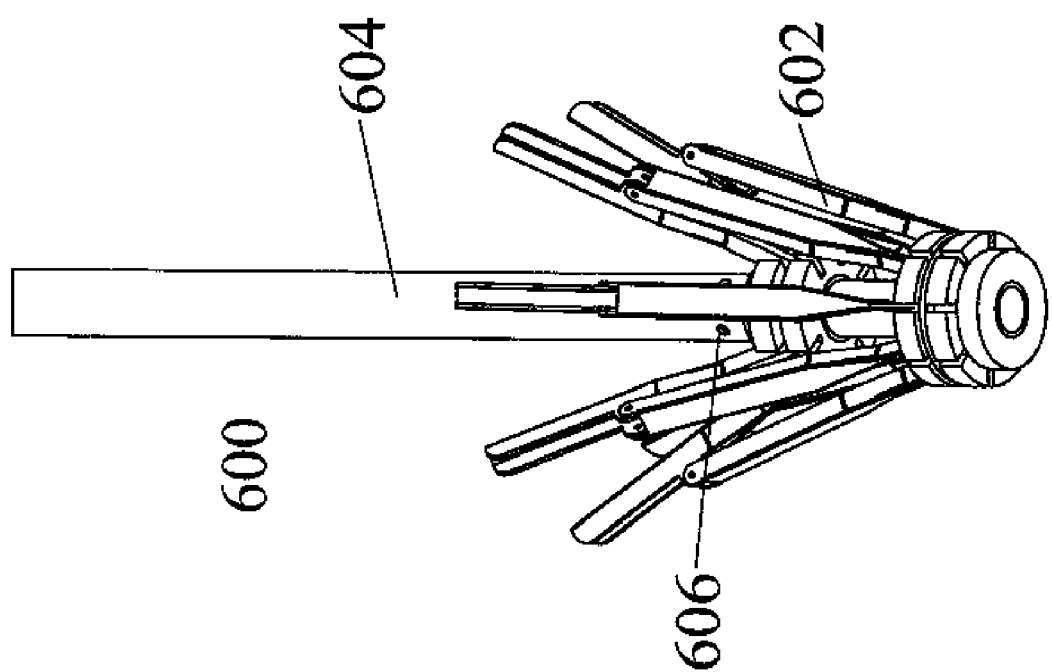
FIGS. 6A and 6B provide detailed views of a suction line and suction inlets that may be used with the devices and methods described here.
Figure 6B:
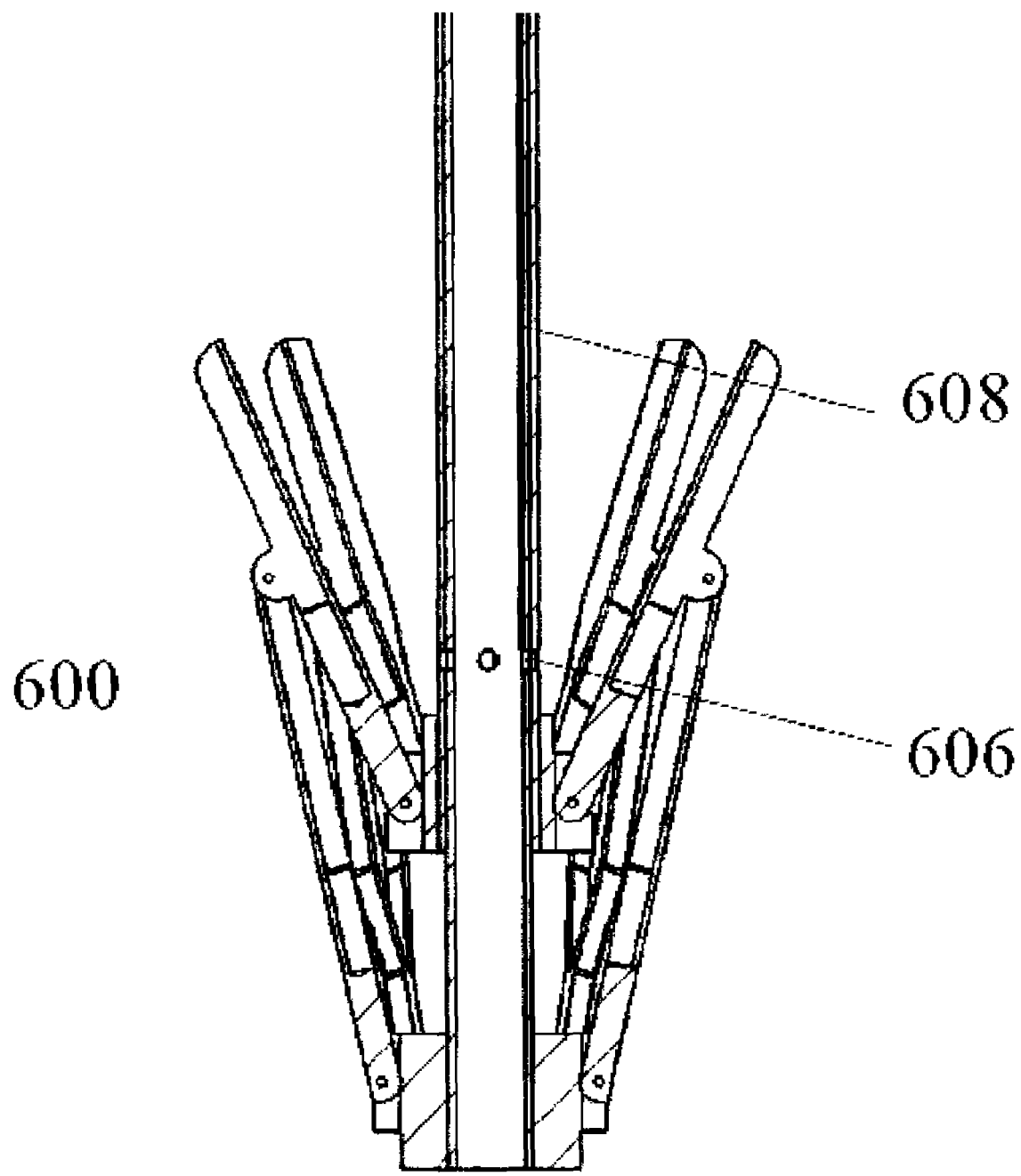

FIGS. 6A and 6B provide more detailed views of the suction line and the suction inlets that may be used with the devices and methods described herein. Specifically, FIG. 6A shows a subassembly (600) of the device comprising an expandable member (602) coupled or attached to a main shaft (604), having one or more suction inlets (606). FIG. 6B provides an exploded cross-sectional view of FIG. 6A, showing suction line (608) and suction inlets (606). As mentioned briefly above, any number of suction lines (608) and suction inlets (606) may be used as desirable, and in variations where the inlets are located about the main shaft (604), the inlets may or may not be uniformly spaced apart. The inlets may have any suitable geometry or pattern along the length. They need not be circular as depicted in FIGS. 6A and 6B. Similar to the anchor introducers, the suction lines may be on the expandable member itself.

Figure 7A:
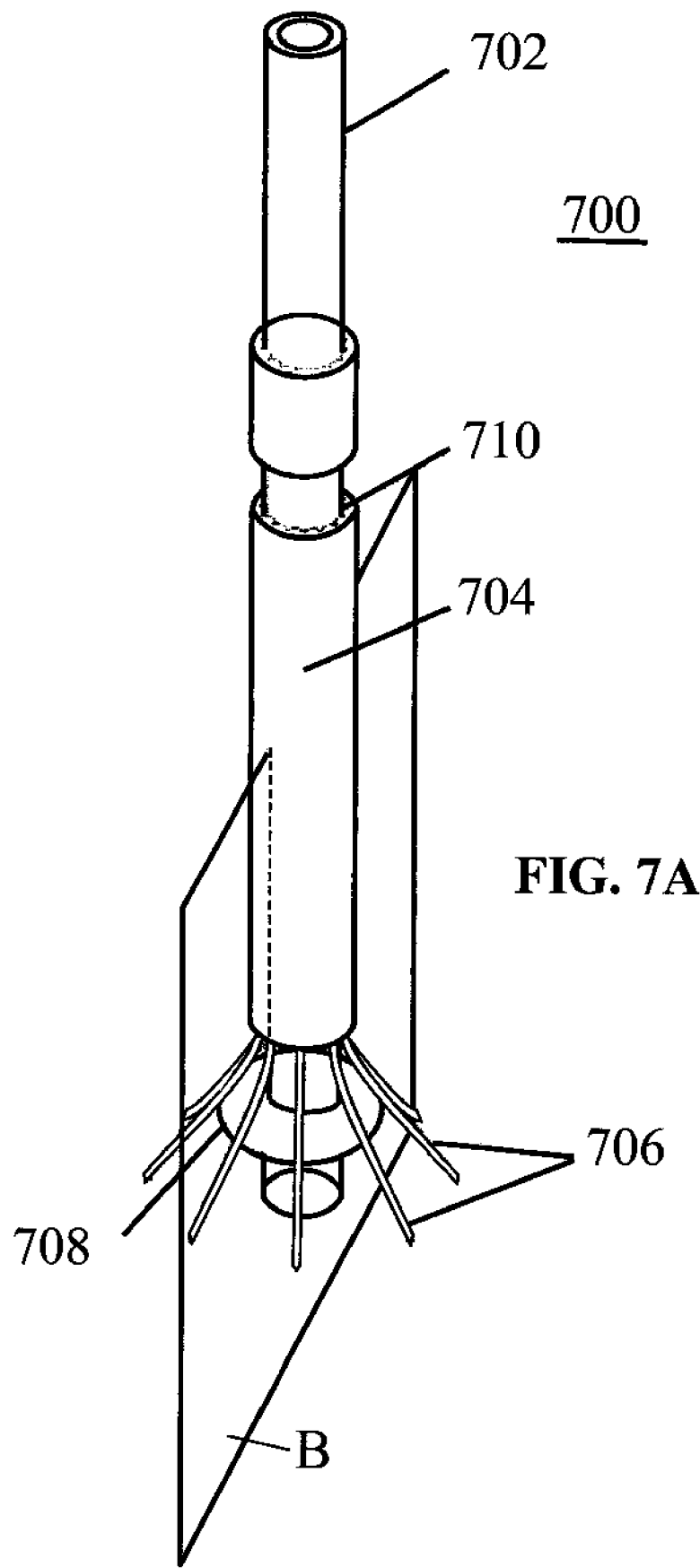
FIG. 7A shows a detailed view of a subassembly of an illustrative device showing anchor introducer grooves, and FIG. 7B provides a cross-sectional view of the device of FIG. 7A, taken along plane B.
Figure 7B:
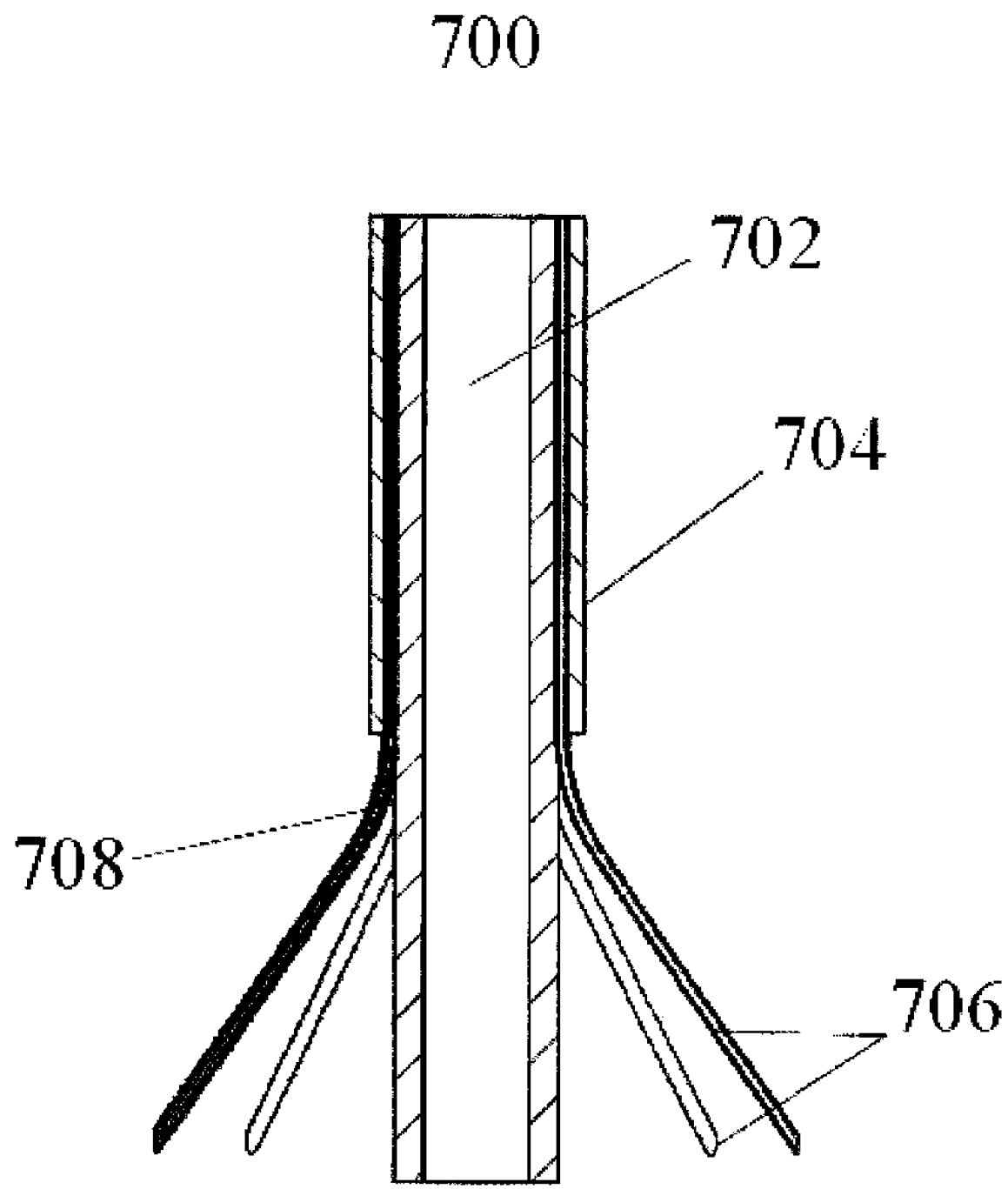

FIG. 7A shows device subassembly (700) comprising shaft (702), holder (704), anchor introducers (706), and anchor introducer expander (708). Also shown in FIG. 7A are grooves (710) in holder (704) for retaining anchor introducers (706). In FIG. 7A, anchor introducer expander (708) is shown as a balloon in its expanding configuration, urging anchor introducers (706) radially outward. FIG. 7B shows a cross-sectional view of FIG. 7A taken along plane B.

Figure 8:
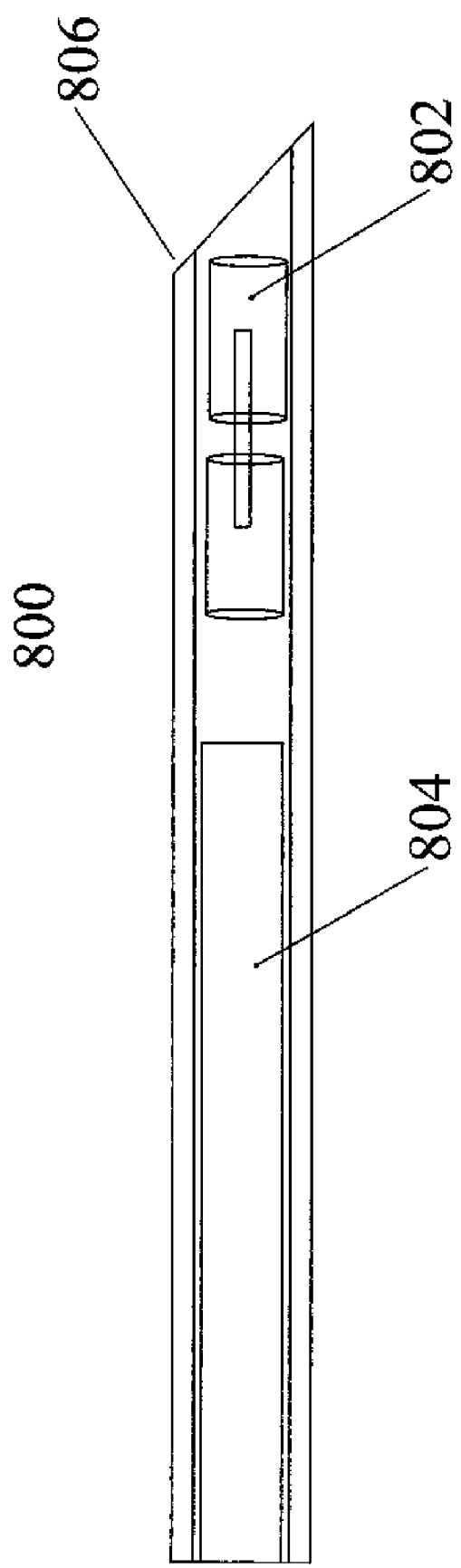
FIG. 8 provides an illustration of how an anchor may be housed within an anchor introducer.

FIG. 8 provides an illustration of how an anchor (in this variation a T-tag, 802) may be housed within anchor introducer (800). In this variation, T-tag (802) is friction fit within the lumen of anchor introducer (800), but other variations are possible. For example, a suture material or the like may be coupled to the anchor. Alternatively, part of the anchor may reside outside a delivery shaft, as common in tagging guns. The anchor may also reside in between a push-rod (804) on the proximal side, and a stopper (not shown) on the distal side. Also shown in FIG. 8 is push-rod (804) for deploying T-tag (802) from distal end (806) of anchor introducer (800), but other anchor deployment mechanisms are possible (e.g., pneumatic, hydraulic, magnetic, or the like). Any suitable number of anchors may be used, and the anchors may be preloaded in the anchor introducer (800), or may be loaded into anchor introducer (800) immediately prior to use. The anchors may also be housed within a replaceable cartridge, and the cartridge preloaded prior to use.

Any suitable anchor geometry may be used. For example, the anchor may be a T-tag, H-tag, V-tag, coil, clip, staple-like anchor, hoop, hook, barb, or the like. In variations where the anchor has one or more anchor ends, the anchor ends may have any suitable shape, e.g., disc, "X-shape," rectangle, etc., and the shapes need not match on all or any ends. In some variations, it may be desirable to increase the surface area of the anchor ends. The anchor may be a single injection-molded piece, or may be comprised of one or more pieces held together by a filament or the like. In these variations, the pieces may be made of the same or different material, and in some variations, the filament is made of a material having a greater elasticity than the anchor ends. The material may be permanent or degradable. In addition, the anchor may also be configured for easy retraction in the event that it is misfired or positioned in a fashion that is otherwise unsatisfactory to the user. In these variations, the anchor may be withdrawn back into the anchor introducer (800), repositioned, and redeployed. Additional anchors may be loaded into the anchor introducer (800) without removing the device from the patient.

Figure 9A:
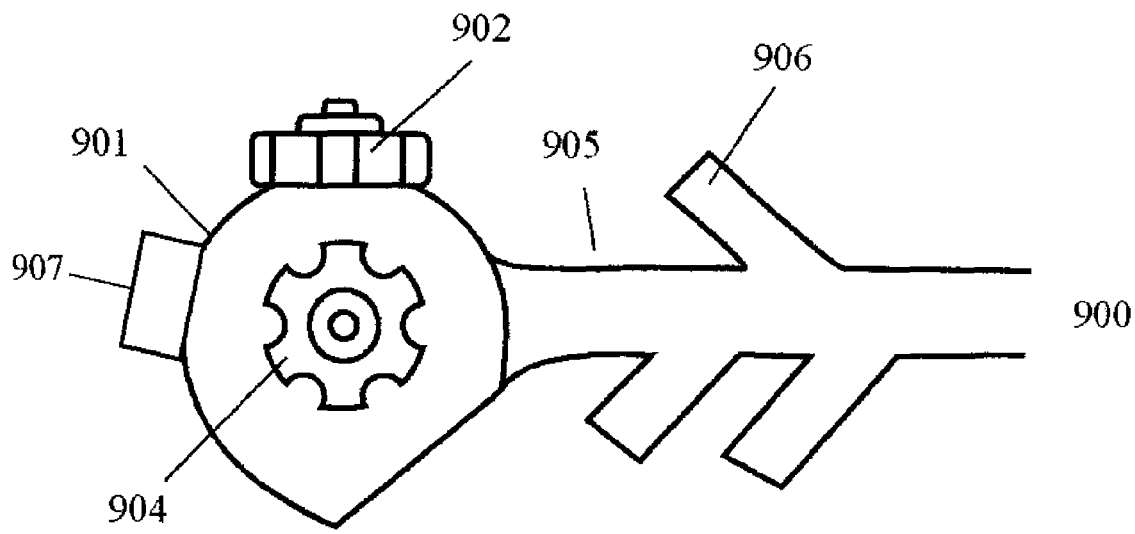
FIGS. 9A-9C depict variations of proximal controls.
Figure 9B:
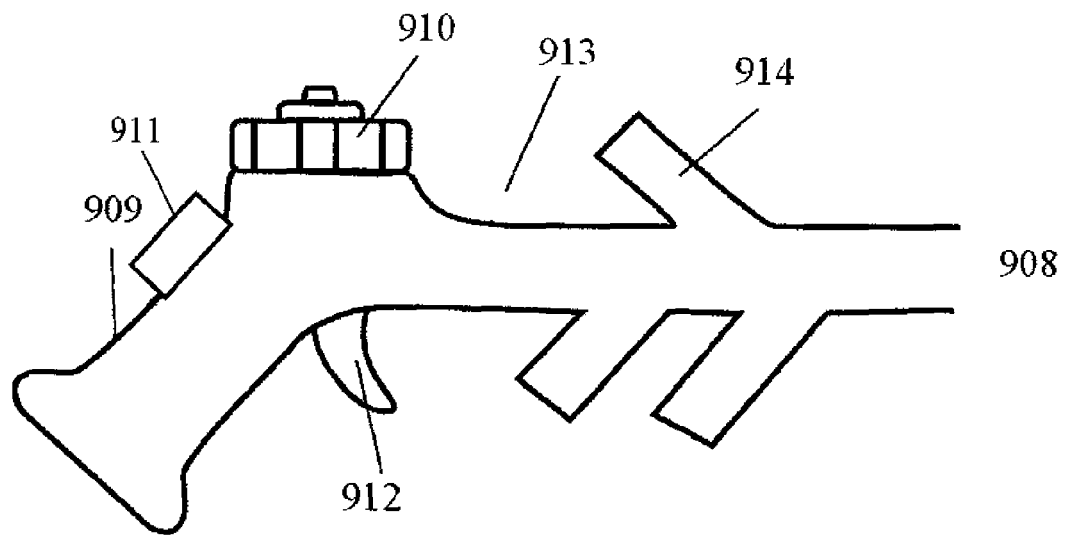
Figure 9C:
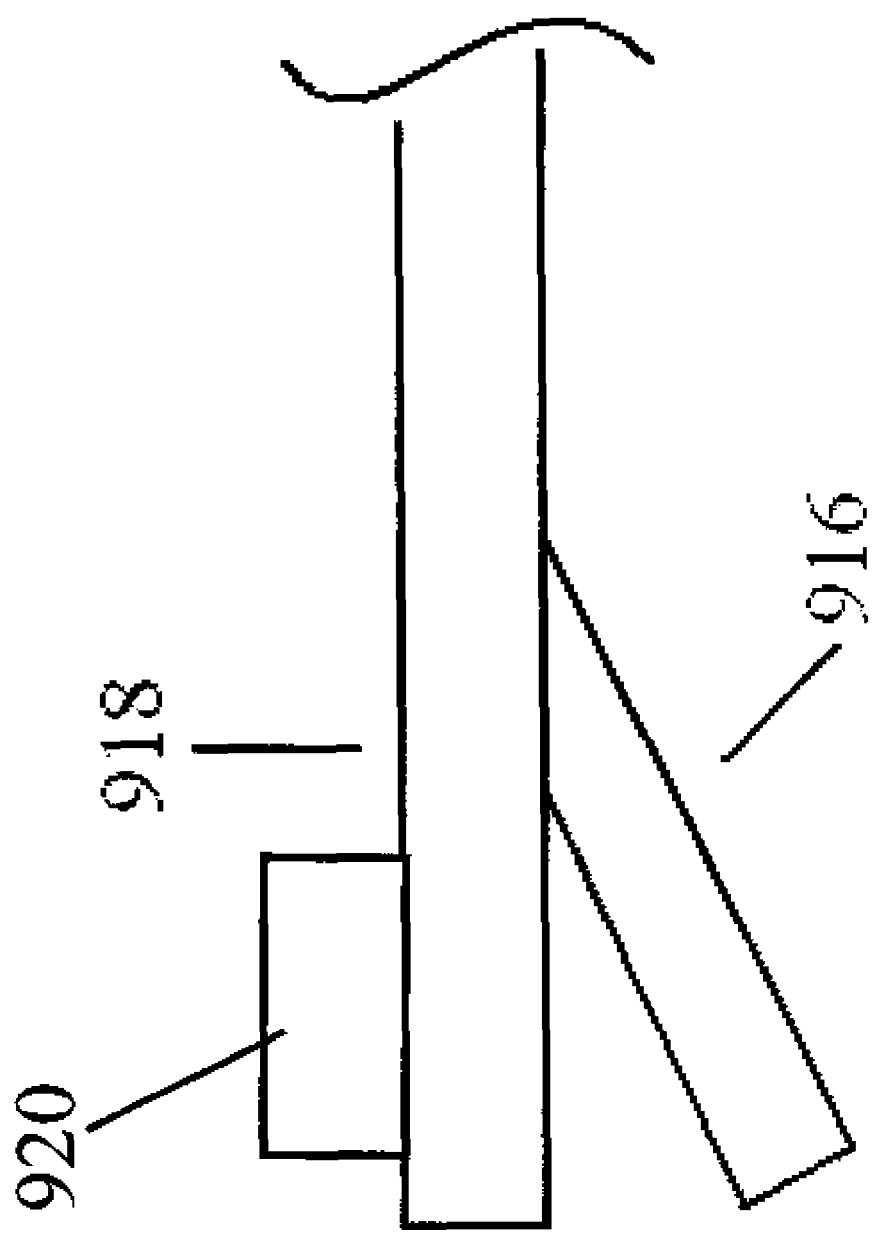

FIGS. 9A-9C show variations of proximal control. Shown in FIG. 9A is proximal portion (900) comprising handle (901) having knobs (902) and (904) thereon. Knob (902) may for example, be used to control the expansion of the expandable member. The knob (902) may be configured for continuous turning, or may be configured to lock periodically as the expandable member reaches various points of expansion. Knob (904) may be used, for example, to actuate or control the push-rod or other actuation mechanism for anchor deployment. Also shown connected to handle (901) is working channel (905) having one or more ports (906) thereon. The additional ports (906) may be used for suction, inflation, or the like. The handle may provide feedback for each step of the procedure via a feedback mechanism (907). The feedback mechanism (907) may provide resistance, pressure force feedback, visualization, auditory, tactile, or any other type of feedback to guide the procedure. FIG. 9B provides a variation (908) similar to the variation provided in FIG. 9A except that knob (904) has been replaced with finger actuated trigger switch (912). Of course, any combination of knobs and triggers, or the like, may be used to actuate or expand the various device components described just above. FIG. 9C shows a variation of proximal control having arms (916 and 918) that may be brought together (e.g., by squeezing action) in order to actuate one or more components of the devices described just above.

III. Methods

Also described here are methods for treating obesity and GERD by intussuscepting a portion of the stomach and securing the intussusception. In some variations the methods comprise creating an intussusception with stomach tissue at a position distal to a gastroesophageal junction using suction, and then deploying one or more anchors through the intussuscepted tissue to secure the intussusception.

Figure 10:
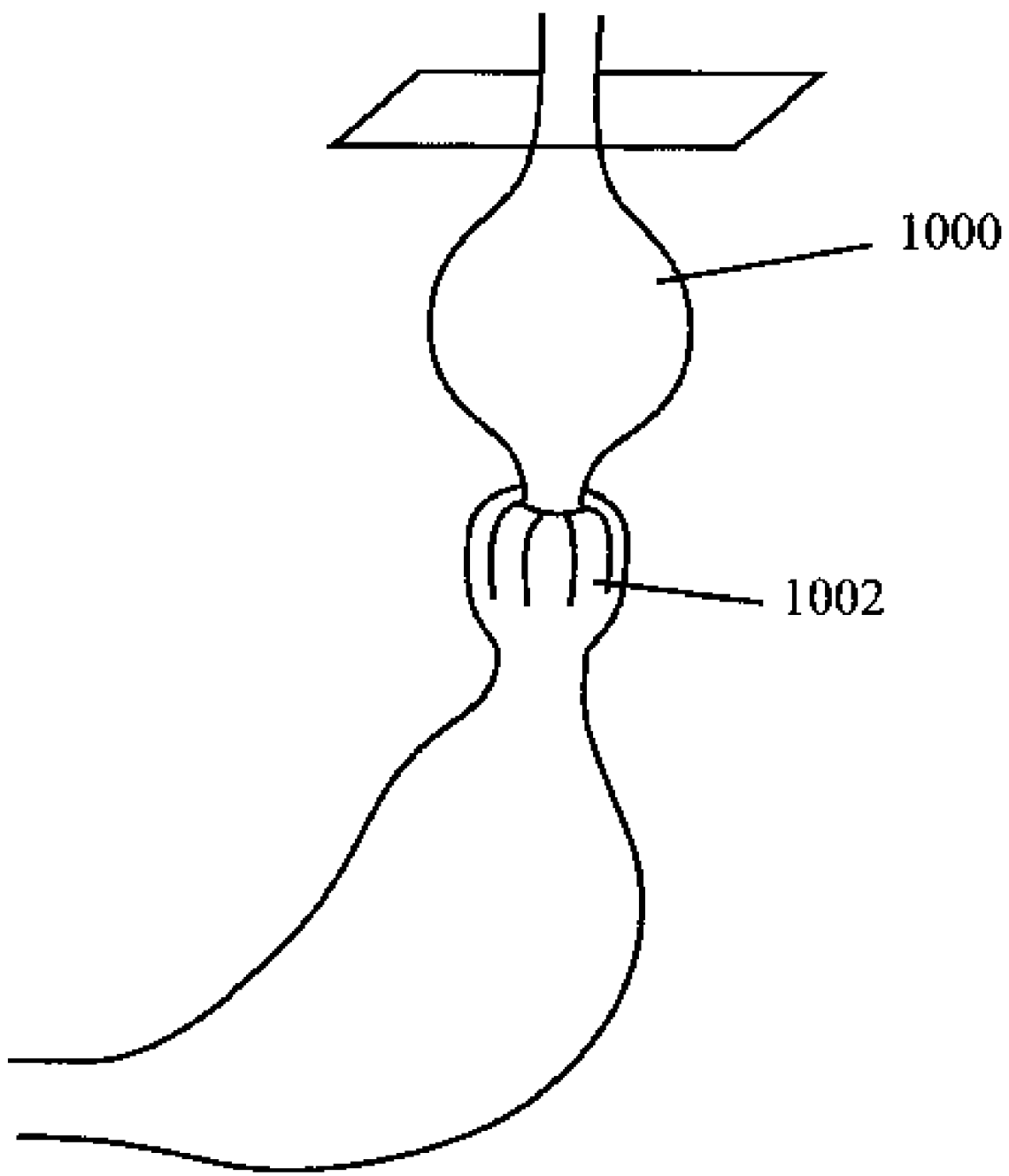
FIG. 10 shows how a pouch is created proximal to intussuscepted tissue, which may be created using the devices and methods described here.

In general, the methods described here are used to create a pouch (1000) proximal to the intussuscepted tissue (1002), as shown in FIG. 10. In this way, a small or reduced stomach space is created (e.g., capable of holding anywhere from 0 cc up to about 100 cc of volume) and food intake will be limited. In addition, creation of a small proximal pouch (1000) may help provide negative reinforcement to over eating, because if too much food is consumed, it will back up into the esophagus, discouraging additional eating. The intussusception may also act as a valve to reduce acid reflux associated with GERD.

Figure 11A:
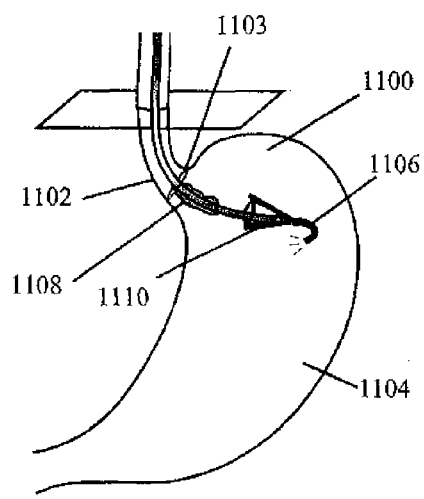

FIGS. 11A-11J depict the creation of an intussusception and a proximal pouch in accordance with the methods described herein. As shown in FIG. 11A, an intussusception device (1100) (such as any of the devices described just above) is advanced transorally through the esophagus (1102) and into the stomach (1104). In some variations, the intussusception device (1100) defines a lumen therethrough, and the device (1100) is advanced over an endoscope (1106). The device (1100) may or may not be advanced simultaneously with the endoscope (1106). For example, in some variations, the device (1100) and endoscope (1106) are advanced in a side-by-side fashion, or are advanced serially, in a non-coupled fashion. The device (1100) may or may not be advanced with a sheath covering a length of the device, as described above.

After the intussusception device (1100) has been advanced to a position adjacent target tissue, the endoscope (1106) is retroflexed to provide visualization of the target tissue (and in some instances the intussusception device itself), as shown in FIG. 11A. Once the intussusception device (1100) has been advanced such that the sizing component (1108) is positioned distal of the gastroesophageal junction (1103), the sizing component (1108) is expanded or otherwise actuated to provide an expanded or second configuration. The sizing component (1108) shown throughout FIG. 11 is an expandable balloon, but as mentioned above with reference to the devices, the sizing component (1108) may be any suitable component capable of preventing the sizing component (1108) from being proximally withdrawn past the gastroesophageal junction (1103). In this way, the sizing component (1108) may be pulled proximally once expanded (e.g., by pulling proximally on intussusception device (1100)), to abut the gastroesophageal junction (1103), in order to facilitate the sizing of a proximal pouch (1000) with sufficient volume capacity. The sizing component (1108) may have any suitable size and be of any suitable shape, as described above. In some variations, the sizing component (1108) is configured to facilitate the sizing of a proximal pouch (1000) capable of retaining a volume anywhere from 0 cc up to about 100 cc of volume. In some variations, the proximal pouch (1000) is sized without the use of a sizing component (1108), for example, by direct visualization of the gastroesophageal junction anatomy, or with the use of a positioner to help ensure proper spacing from the gastroesophageal junction. In some variations, the sizing component (1108) also facilitates placement of the intussusception device (1100) at an advantageous angle within the stomach.

Figure 11B:
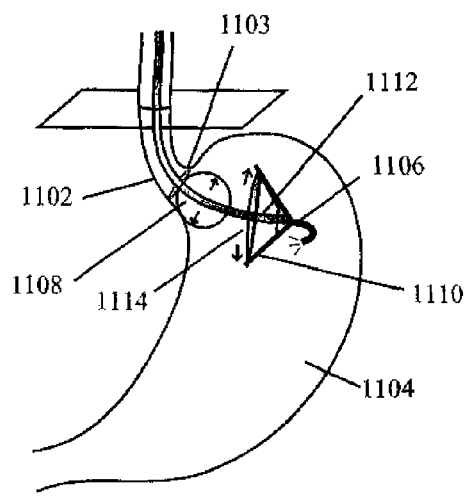
Figure 11C:
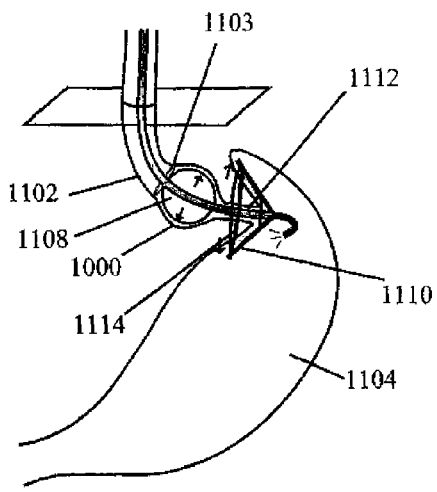
Figure 11D:
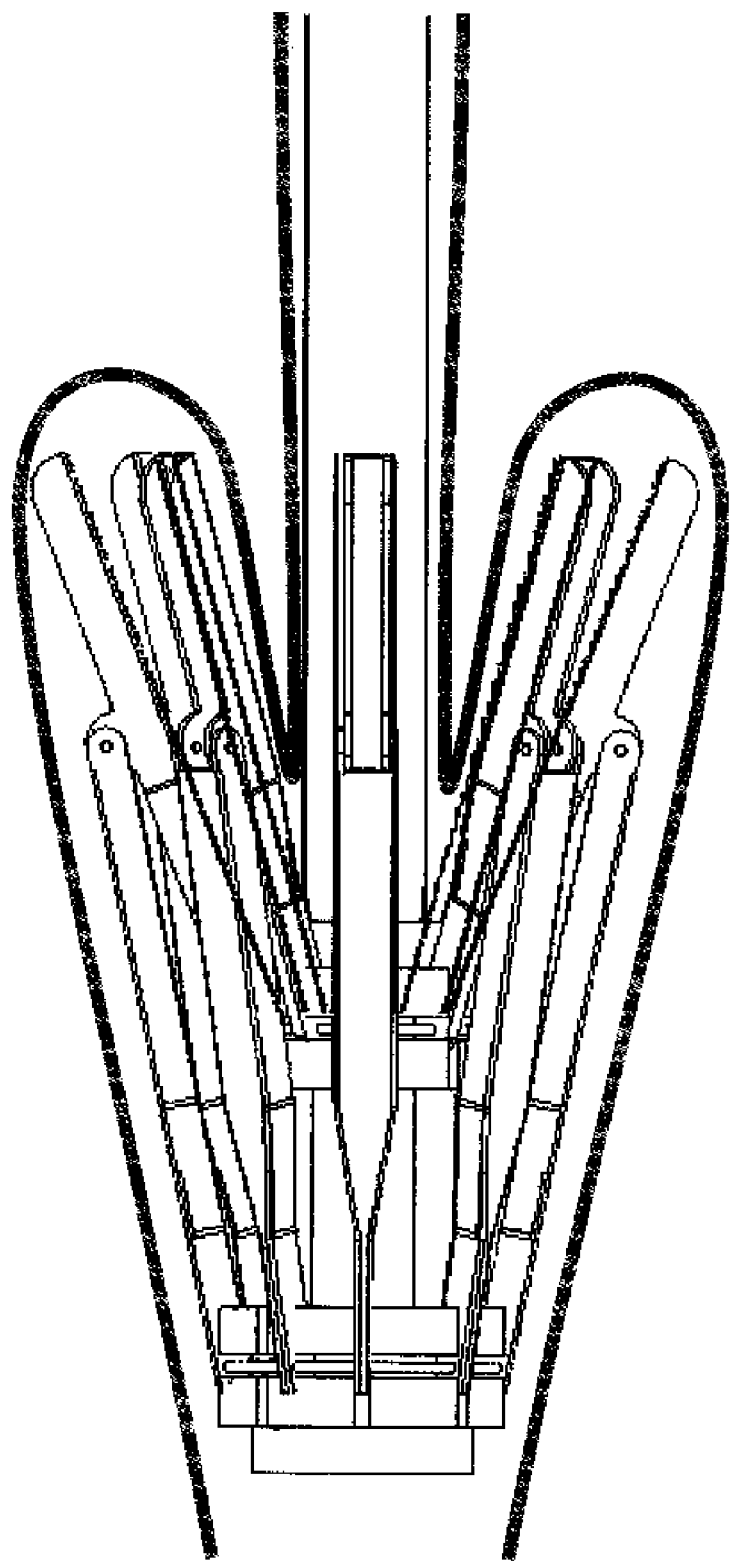

Once the proximal pouch (1000) has been spatially defined (e.g., using a sizing component, positioner, or by direct visualization), an expandable member (1110), such as those described above, is expanded into an expanded configuration as shown in FIG. 11B. In this way, the expandable member defines a proximal cavity (1114) into which the stomach tissue may be pulled, in order to create the intussusception (e.g., using suction). After the expandable member (1110) is expanded, it may be locked in the expanded configuration, but need not be. Suction may then be applied (e.g., via one or more suction inlets) to begin to pull stomach tissue into the proximal cavity (1114) as shown in FIGS. 11C and 11D to create the intussusception. The expandable member (1100) may or may not be adjusted to vary the amount of expansion after suction has begun. The stomach tissue may also be pulled into proximal cavity (1114) by other mechanisms other than suction (e.g., using graspers, hooks, adhesives, etc.). The creation of the intussusception (1002) may or may not be performed in a single step.

Figure 11E:
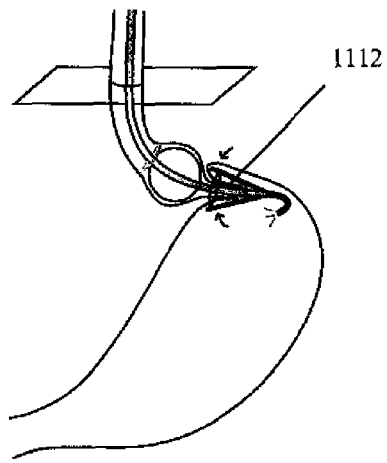

After the intussusception (1002) is created, it may be secured (permanently or temporarily), for example, by deploying one or more anchors through the intussuscepted tissue. In some variations, the anchors are deployed through at least a portion of retaining material (1112), in other variations the anchors are deployed directly through the intussuscepted tissue. As described above, when a retaining material (1112) is used, it may or may not be coupled to the expandable member (1110), and in some variations, the retaining material (1112) is releasably coupled to the expandable member (1110). In this way, positioning of the retaining material (1112) is easily facilitated as shown in FIG. 11E.

Figure 11F:
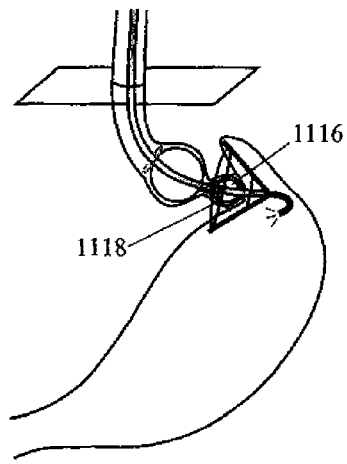
Figure 11G:
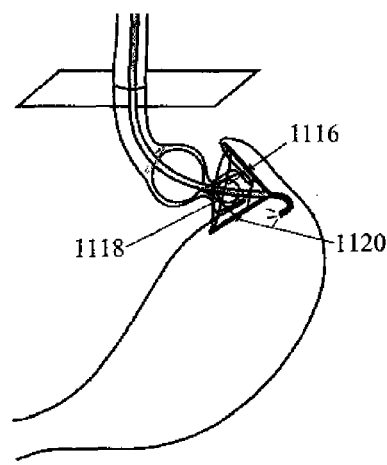
Figure 11H:
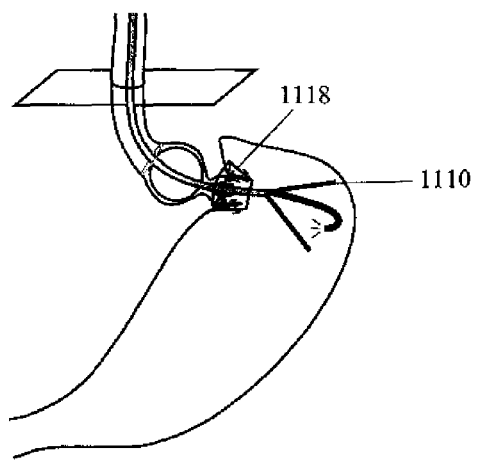

After the retaining material (1112) has been properly positioned about the intussuscepted tissue, an anchor introducer expander (1116) may be expanded to radially expand one or more anchor introducers (1118), as shown in FIG. 11F. As described above, anchor introducers (1118) house one or more anchors (1120) therein for delivery or deployment through the intussuscepted tissue and in variations where it may be desirable, at least a portion of retaining material (1112). After the anchor introducers (1118) are expanded, anchors (1120) are deployed therefrom using any suitable deployment or actuation technique, as shown in FIG. 11G. In some variations, the anchors (1120) are deployed using a push rod (not shown). When a retaining material (1112) is employed, the anchors (1120) pierce through at least a portion of the retaining material (1112) securing the intussusception as shown in FIG. 11H. Safety mechanisms may ensure that neither the anchor introducers (1118) or anchors (1120) go further than the operator desires. These safety mechanisms may include, but are not limited to, a protective portion (not shown) around the expandable member (1110) or guides (not shown) that keep the anchor introducers or anchors at a safe range. The expandable member (1110) may then be hyperextended to a collapsed configuration as shown in FIG. 11H, and after the sizing component (1108) and anchor introducer expander (1118) are returned to their delivery configurations, the device is withdrawn proximally from the body as shown by the arrow in FIG. 11I, leaving the retaining material (1112) and anchors (1120) to secure the intussusception (1002) as shown in FIG. 11J. When a sheath is used, as described above, the sheath may or may not be advanced over the device, before the device is withdrawn.

Figure 12A:
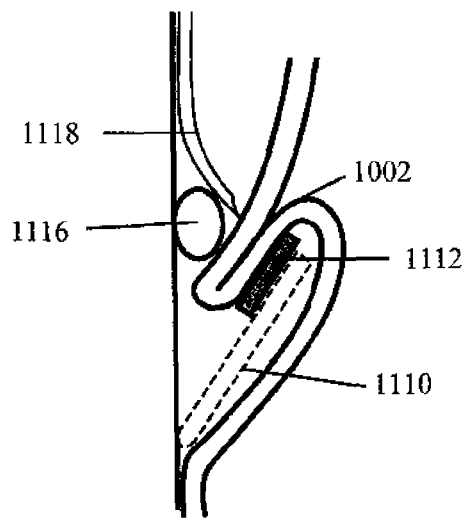
FIGS. 12A-12D depict anchor deployment in accordance with one variation of the methods described here, in more detail.
Figure 12B:
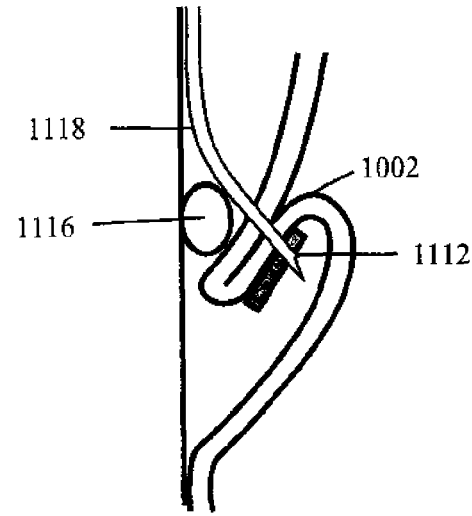
Figure 12C:
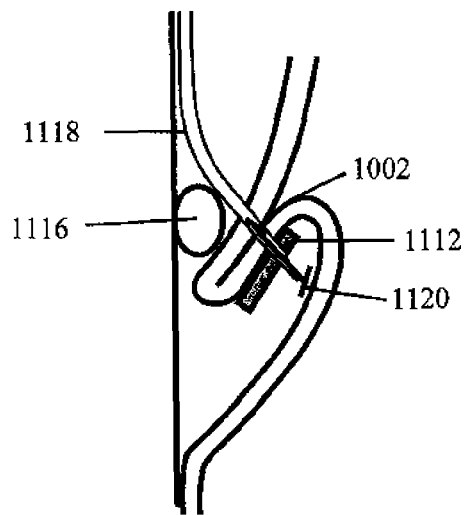
Figure 12D:
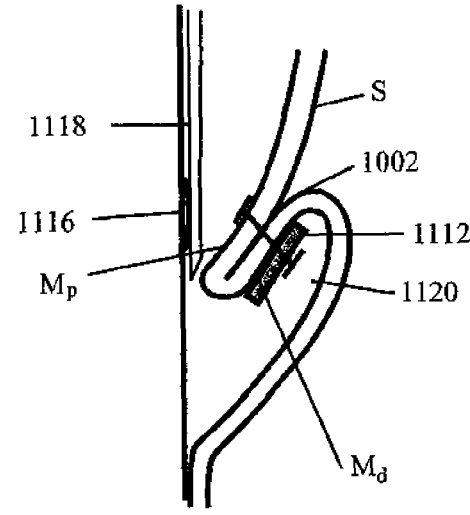

FIGS. 12A-12D depict the anchor deployment in more detail. Shown there is anchor introducer (1118) positioned adjacent the intussusception (1002) as shown in FIG. 12A. The anchor introducer (1118) has been expanded by anchor introducer expander (1116), and is then advanced through intussusception (1002) and at least a portion of retaining material (1112) as shown in FIG. 12B. As mentioned in detail above, the anchor introducer may have a pointed or blunt end, and may be capable of piercing tissue. The anchor introducer may also simply be a conduit for positioning the anchor, or may be a conduit for airflow, which may or may not be used to improve suction. The anchor (1120) is then deployed from the anchor introducer (1118) via its distal end, or an aperture thereon as shown in FIG. 12C. The anchor introducer is then collapsed and withdrawn (e.g., when the intussusception device is withdrawn) leaving the anchor to secure the intussusception, as shown in FIG. 12D. The intussusception creates a serosal (S) to serosal (S) contact surface through which the anchor is deployed, helping to ensure that the intussusception is properly secured. It should be understood, that at each step of the method just described, feedback mechanisms (e.g., resistance, pressure force feedback, visualization, auditory, tactile, etc.) may be used to guide the procedure.

While the methods described here depict a single retaining material for apposition against a distal mucosal surface ($M_d$), a retaining material may be placed against the proximal mucosal surface ($M_p$) of the intussuscepted tissue as well, and as described above, in some variations, no retaining material is used. It should be understood that while the anchor (1120) shown in FIGS. 12C and 12D is a T-tag having ends that expand from a reduced profile delivery configuration to form cross-bars, the anchors may have any suitable shape as described above. When T-tags are used, an alternative deployment mechanism is to mimic the use of a tagging gun. In this variation, an end of an anchor could be expanded on the proximal mucosal surface ($M_p$), and the anchor introducer expander (1116) then advanced through the intussusception (1002) and at least a portion of the retaining material (1112). The distal portion of the anchor may then be deployed from the anchor introducer (1118) to secure the intussusception (1002).

In some variations, it may be advantageous to minimize the pressure applied to the stomach walls. This may help reduce pressure necrosis and help facilitate long-term placement of the anchors. Also, to avoid complete obstruction at the intussusception due to post-surgical swelling, a retaining material may be used on the distal mucosal surface, and may have a looser configuration at deployment to allow for post-procedure tissue swelling that may occur as a result of the tissue manipulation. The retaining material may also be adjusted or removed (e.g., at a follow-up visit), in accordance with the descriptions above, to change the aperture size of the gastric stricture.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What we claim is:

1. A method for treating obesity by intussuscepting a portion of a stomach comprising:
   transorally advancing a device to a position inside the stomach, the device having a proximal portion and a distal portion, the distal portion comprising an expandable member and a material covering at least a portion of the expandable member, the expandable member having a proximal end, distal end, inner surface, and outer surface, and defining a cavity therein to receive tissue;

expanding the expandable member, such that the proximal end of the expanded expandable member defines a proximal end of the cavity;

drawing stomach tissue through the proximal end of the cavity into a distal portion of the cavity of the expanded expandable member using suction to telescope a first region of stomach tissue into a second region of stomach tissue, thereby forming an intussusception and a stomach portion proximal to the intussusception and distal to a gastroesophageal junction; and deploying one or more anchors through the intussusception to secure the intussusception.

2. The method of claim 1 wherein the intussusception is created in a single step.

3. The method of claim 1 wherein the anchors are deployed through the intussusception simultaneously.

4. The method of claim 1 further comprising positioning one or more anchors adjacent to the intussusception prior to deploying the one or more anchors.

5. The method of claim 4 wherein the one or more anchors are positioned simultaneously.

6. The method of claim 1 further comprising positioning at least one retaining material adjacent to the intussusception prior to deploying one or more anchors through the intussusception, wherein the one or more anchors are further deployed through at least a portion of the retaining material.

7. The method of claim 1 wherein the stomach portion is capable of retaining from about 0 cc up to about 100 cc in volume.

8. The method of claim 7 wherein the position of the intussusception is determined using a sizing component.

9. The method of claim 1 wherein the intussusception is created with the aid of a feedback mechanism.

10. A method for treating obesity by intussuscepting a portion of a stomach comprising:

transorally advancing a device to a position inside the stomach distal to a gastroesophageal junction, wherein the device has a proximal portion and a distal portion, the distal portion comprising an expandable member, a material covering at least a portion of the expandable member, and a suction inlet, the expandable member having a proximal end, distal end, inner surface, and outer surface, and defining a cavity therein to receive tissue;

expanding the expandable member, such that the proximal end of the expanded expandable member defines a proximal end of the cavity;

drawing stomach tissue through the proximal end of the cavity into a distal portion of the cavity of the expanded expandable member using suction to telescope a first region of stomach tissue into a second region of stomach tissue, thereby forming an intussusception and a stomach portion proximal to the intussusception and distal to a gastroesophageal junction; and securing the intussusception.

11. The method of claim 10 wherein the device further comprises one or more anchor introducers having one or more anchors therein and the method further comprises deploying the one or more anchors to secure the intussusception.

12. The method of claim 11 wherein securing the intussusception using the one or more anchors further comprises deploying the one or more anchors through at least a portion of at least one retaining material.

13. The method of claim 12 wherein the at least one retaining material is positioned about at least a portion of the expandable member.

14. The method of claim 11 wherein the one or more anchors are deployed simultaneously.

15. The method of claim 11 further comprising positioning one or more anchors adjacent to the intussusception prior to deploying the one or more anchors.

16. The method of claim 15 wherein the one or more anchors are positioned simultaneously.

17. The method of claim 10 wherein the stomach portion is capable of retaining from about 0 cc up to about 100 cc in volume.

18. The method of claim 17 wherein the position of the intussusception is determined using a sizing component.

19. The method of claim 10 wherein the intussusception is created with the aid of a feedback mechanism.

* * * * *